(12) United States Patent
Keller et al.

(10) Patent No.: US 9,994,821 B2
(45) Date of Patent: Jun. 12, 2018

(54) METHODS FOR ENRICHING PLURIPOTENT STEM CELL-DERIVED CARDIOMYOCYTE PROGENITOR CELLS AND CARDIOMYOCYTE CELLS BASED ON SIRPA EXPRESSION

(75) Inventors: Gordon Keller, Toronto (CA); April M. Craft, Toronto (CA); Nicole C. Dubois, Toronto (CA)

(73) Assignee: UNIVERSITY HEALTH NETWORK (CA)

( * ) Notice: Subject to any disclaimer, the term of this patent is extended or adjusted under 35 U.S.C. 154(b) by 111 days.

(21) Appl. No.: 13/819,318

(22) PCT Filed: Aug. 26, 2011

(86) PCT No.: PCT/CA2011/000965
§ 371 (c)(1),
(2), (4) Date: May 13, 2013

(87) PCT Pub. No.: WO2012/024782
PCT Pub. Date: Mar. 1, 2012

(65) Prior Publication Data
US 2013/0230921 A1 Sep. 5, 2013

Related U.S. Application Data

(60) Provisional application No. 61/377,665, filed on Aug. 27, 2010.

(51) Int. Cl.
C12N 5/00 (2006.01)
C12N 5/071 (2010.01)
G01N 33/53 (2006.01)
C12N 5/077 (2010.01)
C12Q 1/68 (2018.01)
G01N 33/569 (2006.01)
G01N 33/50 (2006.01)

(52) U.S. Cl.
CPC ......... *C12N 5/0657* (2013.01); *C12Q 1/6881* (2013.01); *C12N 2501/115* (2013.01); *C12N 2501/155* (2013.01); *C12N 2501/16* (2013.01); *C12N 2501/165* (2013.01); *C12N 2501/415* (2013.01); *C12N 2506/00* (2013.01); *C12N 2506/02* (2013.01); *C12N 2506/45* (2013.01); *C12Q 2600/158* (2013.01); *G01N 33/5073* (2013.01); *G01N 33/53* (2013.01); *G01N 33/56966* (2013.01)

(58) Field of Classification Search
CPC .............. C12N 5/0657; C12N 2506/00; C12N 2506/02; C12N 2506/45; C12N 33/56966; G01N 33/53; G01N 33/5073
USPC .......................................... 435/7.1, 366, 377
See application file for complete search history.

(56) References Cited

U.S. PATENT DOCUMENTS

2005/0054092 A1 3/2005 Xu et al.
2005/0214873 A1 9/2005 Buehring et al.
2012/0288481 A1* 11/2012 Anversa et al.

FOREIGN PATENT DOCUMENTS

| EP | 1254952 A1 | 11/2002 |
|---|---|---|
| JP | WO01/048151 A1 | 7/2001 |
| JP | 2003-506075 A | 2/2003 |
| JP | 2007-529227 A | 10/2007 |
| WO | 01/11011 A2 | 2/2001 |
| WO | 2003/046141 A2 | 6/2003 |
| WO | 2005/090558 A1 | 9/2005 |
| WO | 2009017460 A1 | 2/2009 |
| WO | 2012162741 A1 | 12/2012 |

OTHER PUBLICATIONS

Allegrucci et al., 2006, Human Reproduction Update, vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Burridge et al., 2011, PLoS One, vol. 6, No. 4, e18293, p. 1-16.*
Zhang et al., 2009, Circulation Research, vol. 104, p. e30-e41, published online Feb. 12, 2009.*
Martins et al., 2014, Stem Cell Rev and Rep, vol. 7, p. 177-190.*
Uosaki et al., 2011, PLoS One, vol. 6, No. 8, e23657, p. 1-9.*
Laflamme et al., 2007, Nature Biotechnology, vol. 25, No. 9, p. 1015-1024.*
Kattman et al., 2011, Cell Stem Cell, vol. 8, p. 228-240.*
International Search Report and Written Opinion for PCT International Application No. PCT/CA2011/000965 dated Nov. 15, 2011.
Yang et al., Human cardiovascular progenitor cells develop from a KDR+embryonic-stem-cell-derived populiation, Nature, vol. 453, p. 524-528, May 22, 2008.
Bearzi, C. et al., Human cardiac stem cells, Proc Natl Acad Sci, vol. 104, p. 14068-14073, Aug. 28, 2007.
Hattori, F. et al., Nongenetic method for purifying stem cell-derived cardiomyocytes, Nat Methods, vol. 7, p. 61-66, Jan. 2010.
Huber, I. et al., Identification and selection of cardiomyocrytes during human embryonic stem cell differentiation, FASEB J., vol. 21, p. 2551-2563, Aug. 2007.
Supplementary European Search Report for EP 11819236.8 dated Jan. 10, 2014.
Xu, Chunhui et al., Characterization and enrichment of cardiomyocytes derived from human embryonic stem cells, Circulation Research, vol. 91, No. 6, p. Sep. 20, 2002, p. 501-508.
Dubois, N. et al., SIRPA is a specific cell-surface marker for isolating cardiomyocytes derived from human pluripotent stem cells, Nature Biotechnology, vol. 29, No. 11, p. 1011-1018, Nov. 1, 2011.
Elliot, D. et al., NKX2-5eGFP/whESCs for isolation of human cardiac progenitors and cardiomyocytes, Nature Methods, vol. 8, No. 12, p. 1037-1040, Oct. 23, 2011.

(Continued)

*Primary Examiner* — Shin Lin Chen
(74) *Attorney, Agent, or Firm* — J.A. Lindeman & Co., PLLC

(57) ABSTRACT

The present invention relates to in vitro methods of enriching populations of human pluripotent stem cells that are induced to differentiate to cardiomyocyte progenitor cells and cardiomyocyte cells. The cell populations can be enriched by isolating cells that express SIRPA. The invention also related to in vitro-enriched populations of cardiomyocyte cells and cardiomyocyte progenitor cells obtained from populations of pluripotent stem.

12 Claims, 15 Drawing Sheets

(56) References Cited

OTHER PUBLICATIONS

Office Action—English translation of corresponding Japanese Patent Application No. 2013-525094, dated Sep. 8, 2015.

* cited by examiner a

|  | Total cell# | SIRPA- cell# | SIRPA- (%) | SIRPA- exp cell# | Eff SIRPA- | Eff SIRPA - (%) |
|---|---|---|---|---|---|---|
| E1 | 5920000 | 844000 | 31.28 | 1851776 | 0.45577867 | 45.57786687 |
| E2 | 3070000 | 594670 | 32.98 | 1012486 | 0.58733652 | 58.73365163 |
| E3 | 2200000 | 372940 | 33.57 | 738540 | 0.50496926 | 50.49692637 |
| E4 | 6980000 | 1380000 | 34.08 | 2378784 | 0.58012833 | 58.01283345 |
| E5 | 34900000 | 4700000 | 20.42 | 7126580 | 0.65950288 | 65.95028752 |
| E6 | 14200000 | 2590000 | 50.5 | 7171000 | 0.36117696 | 36.11769628 |
| E7 | 17100000 | 3650000 | 36.12 | 6176520 | 0.59094765 | 59.09476534 |
| E8 | 15390000 | 476000 | 5.24 | 806436 | 0.59025143 | 59.02514273 |
| Average |  |  |  |  |  | 54.12614627 | b

|  | Total cell# | SIRPA+ cell# | SIRPA+ (%) | SIRPA+ exp cell# | Eff SIRPA+ | Eff SIRPA+ (%) |
|---|---|---|---|---|---|---|
| E1 | 5920000 | 419000 | 31.3 | 1852960 | 0.22612469 | 22.6124687 |
| E2 | 3070000 | 163830 | 10.17 | 312219 | 0.52472784 | 52.47278353 |
| E3 | 2200000 | 93300 | 8.56 | 188320 | 0.49543331 | 49.5433305 |
| E4 | 6980000 | 461000 | 30.08 | 2099584 | 0.2195673 | 21.95673048 |
| E5 | 34900000 | 1640000 | 17.79 | 6208710 | 0.26414505 | 26.41450478 |
| E6 | 14200000 | 299000 | 10.8 | 1533600 | 0.19496609 | 19.49660929 |
| E7 | 17100000 | 1930000 | 32.98 | 5639580 | 0.34222407 | 34.22240663 |
| E8 | 15390000 | 4650000 | 65.15 | 10026585 | 0.46376708 | 46.37670752 |
| E9 | 14800000 | 3600000 | 55.23 | 8174040 | 0.44041869 | 44.04186914 |
| Average |  |  |  |  |  | 35.23749006 |

Figure 21 a

| total cell# | LIN- cell# | LIN- (%) | LIN- exp cell# | Eff LIN- | Eff LIN- (%) |
|---|---|---|---|---|---|
| 10800000 | 2770000 | 78.65 | 8494200 | 0.32610487 | 32.6104872 |
| 5850000 | 531100 | 21.73 | 1271205 | 0.41779257 | 41.7792567 |
| 14000000 | 1110000 | 18.12 | 2536800 | 0.43755913 | 43.755913 |
| 26000000 | 2350000 | 26.73 | 6949800 | 0.33813923 | 33.8139227 |
| 15080000 | 3430000 | 51.31 | 7737548 | 0.44329289 | 44.3292888 |
| 10300000 | 3000000 | 47.89 | 4932670 | 0.60818988 | 60.8189885 |
| average | | | | | 42.8513095 | b

| total cell# | LIN+ cell# | LIN+ (%) | LIN+ exp cell# | Eff LIN+ | Eff LIN+ (%) |
|---|---|---|---|---|---|
| 10800000 | 680000 | 10.32 | 1114560 | 0.61010623 | 61.010623 |
| 5850000 | 157700 | 5.48 | 320580 | 0.49192089 | 49.1920893 |
| 14000000 | 1360000 | 20.42 | 2858800 | 0.47572408 | 47.572408 |
| 26000000 | 3810000 | 38.55 | 10023000 | 0.38012571 | 38.0125711 |
| 15080000 | 1960000 | 21.37 | 3222596 | 0.60820531 | 60.820531 |
| 10300000 | 2200000 | 35.9 | 3697700 | 0.59496444 | 59.4964437 |
| average | | | | | 52.684111 |

METHODS FOR ENRICHING PLURIPOTENT STEM CELL-DERIVED CARDIOMYOCYTE PROGENITOR CELLS AND CARDIOMYOCYTE CELLS BASED ON SIRPA EXPRESSION

RELATED APPLICATIONS

This application is a National Phase filing under 35 U.S.C. § 371 of International Application PCT/CA2011/000965, with an International Filing Date of Aug. 26, 2011, which claims priority from U.S. Provisional Patent Application No. 61/377,665 filed on Aug. 27, 2010, the contents of each are incorporated herein by reference in its entirety.

FIELD OF THE INVENTION

The present invention relates to methods for enriching pluripotent stem cell-derived cardiomyocyte progenitor cells and cardiomyocyte cells based on SIRPA expression.

BACKGROUND OF THE INVENTION

The potential of human embryonic (hESCs) and induced pluripotent stem cells (hiPSCs) to generate cardiovascular cells in culture provides a powerful model system for investigating cellular interactions and molecular regulators that govern the specification, commitment and maturation of these lineages, as well as a unique and unlimited source of human cardiomyocytes for drug testing and regenerative medicine strategies[1-4]. Translating this remarkable potential into practice is, however, dependent on technologies that enable the reproducible generation of highly enriched populations of cardiomyocytes, as contaminating cell types could impact drug responses and other functional properties in vitro and increase the risk for abnormal growth and teratoma formation following transplantation in vivo[5]. When induced under optimal cardiac conditions, human pluripotent stem cells (hPSCs) will efficiently differentiate to generate mixed cardiovascular populations, including cardiomyocytes, smooth muscle cells, fibroblasts and endothelial cells[3]. While cardiomyocytes can represent up to 70% of the population for any given hPSC line, the efficiency of generating this lineage does vary considerably between different stem cell lines. Further manipulation of induction conditions has not yet yielded strategies for the generation of pure populations of cardiomyocytes from a broad range of hPSC lines.

To enrich for cardiomyocytes from the differentiation cultures, cardiomyocyte-specific fluorescent reporters or drug selectable elements have been introduced into hPSCs[6-8]. Following differentiation, cardiomyocytes can be enriched either by fluorescent-activated cell sorting (FACS) or the addition of appropriate selection drugs. Although these strategies do allow for the generation of enriched cardiomyocyte populations, they suffer from a major drawback as a reporter vector must be introduced into each hPSC line used, resulting in genetically modified cardiomyocytes, thus reducing their utility for clinical applications. In a more recent study, Hattori et al. demonstrated that it was possible to isolate cardiomyocytes by FACS, based on their high mitochondrial content[9]. While this approach appears to be useful for isolating mature cardiomyocytes, cells with fewer mitochondria, such as immature hPSC-derived cardiomyocytes, may be more difficult to distinguish from other cell types.

SUMMARY OF THE INVENTION

In an aspect, there is provided a method of enriching a population of cells for cardiomyocyte cells and cardiomyocyte progenitor cells comprising providing the population of cells from which cardiomyocyte cells and cardiomyocyte progenitor cells are to be isolated; and isolating from the population, cells expressing SIRPA; wherein the population of cells comprises a population of human pluripotent stem cells induced to differentiate into cardiomyocyte cells and cardiomyocyte progenitor cells.

In a further aspect, there is provided an enriched population of cardiomyocyte cells and cardiomyocyte progenitor cells obtained using any one of the methods described herein.

In a further aspect, there is provided an isolated population of cells enriched for cardiomyocyte cells and cardiomyocyte progenitor cells, wherein the population of cells comprises at least 60%, preferably at least 90%, cardiomyocyte cells and cardiomyocyte progenitor cells.

In a further aspect, there is provided the use of SIRPA for isolating cardiomyocyte cells and cardiomyocyte progenitor cells from a population of cells, wherein the population of cells comprise a population of human pluripotent stem cells induced to differentiate into cardiomyocyte cells and cardiomyocyte progenitor cells.

In a further aspect, there is provided a method of depleting a population of cells for cardiomyocyte cells and cardiomyocyte progenitor cells comprising: providing the population of cells from which cardiomyocyte cells and cardiomyocyte progenitor cells are to be depleted; and depleting from the population, cells expressing SIRPA; wherein the population of cells comprises a population of human pluripotent stem cells induced to differentiate into cardiomyocyte cells, cardiomyocyte progenitor cells, and non-cardiomyocytes.

In a further aspect, there is provided a method of enriching a population of cells for cardiomyocyte cells and cardiomyocyte progenitor cells comprising: providing the population of cells from which cardiomyocyte cells and cardiomyocyte progenitor cells are to be isolated; and depleting from the population, cells expressing at least one of CD90, CD31, CD140B and CD49A; wherein the population of cells comprise a population of human pluripotent stem cells induced to differentiate into cardiomyocyte cells, and cardiomyocyte progenitor cells, and non-cardiomyocytes.

DESCRIPTION OF THE DRAWINGS

Embodiments of the invention may best be understood by referring to the following description and accompanying drawings. In the drawings.

Unstained control of EB-derived cells at day20 of differentiation. (d) Flow cytometric analysis of day20 EB-derived cells with the SIRPA-PE-Cy7 antibody and the corresponding IgG control. (e) Flow cytometric analysis of day20 EB-derived cells with the SIRPA-biotin/Streptavidin-APC (SIRPA-bio/SA-APC) antibody combination, the corresponding IgG control and secondary antibody only staining. (f) Comparison of cell size between SIRPA− and SIRPA+ cell populations (from (e)) by FSC and SSC.

Figure 11:

FIG. 11 shows Western Blot analysis and confirmation of the specificity of the SIRPA antibody. (a) Western Blot analysis of 3 samples from day20 (d20) differentiation cultures compared to undifferentiated ES cells (d0). The SIRPA SE5A5 antibody was used and Ponceau staining is shown for loading control. (b) Co-immunoprecipitation with the SIRPA SE5A5a antibody with controls. SIRPA runs at the predicted size, as previously described and analyzed in Timms et al., 1999.

Figure 12:
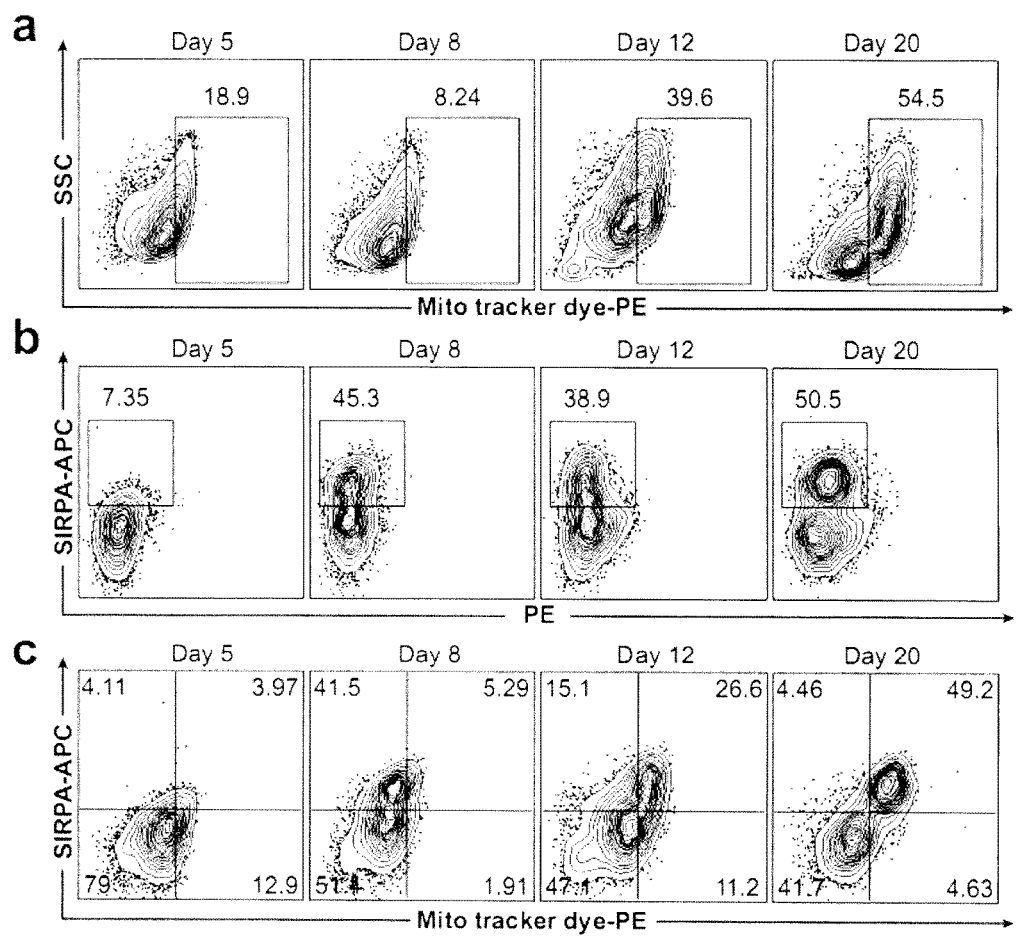

FIG. 12 shows a comparison of SIRPA antibody staining with mito tracker dye retention labelling. (a) Flow cytometric analysis of mito tracker dye labelling at day 5, 8, 12 and 20 of differentiation from HES2 hESCs. (b) Flow cytometric analysis of SIRPA at day 5, 8, 12 and 20 of differentiation from HES2 hESCs. (c) Co-staining of SIRPA and mito tracker dye labelling followed by flow cytometric analysis at day 5, 8, 12 and 20 of differentiation from HES2 hESCs.

Figure 13:
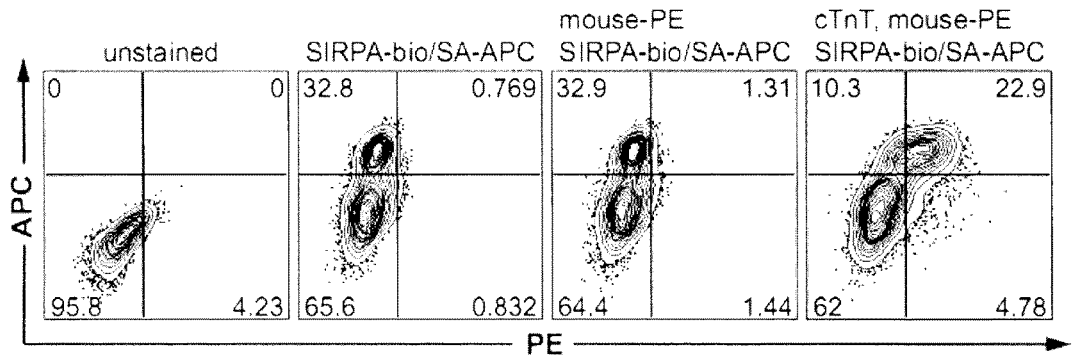

FIG. 13 shows co-expression of SIRPA and cTNT. Cells were stained for SIRPA first, then fixed (4% PFA, 20 min), followed by intracellular staining for cTNT. Since both primary antibodies have been raised in mouse, appropriate controls are shown as well. Cells were stained for anti-SIRPA-biotin/Streptavidin-APC (SIRPA single stain), anti-SIRPA-biotin/Streptavidin-APC and anti-mouse-PE (control to demonstrate that the secondary antibody for cTNT does not recognize SIRPA after fixation), anti-SIRPA-biotin/Streptavidin-APC and anti-cTNT and anti-mouse-PE (SIRPA and cTNT co-staining).

Figure 14:
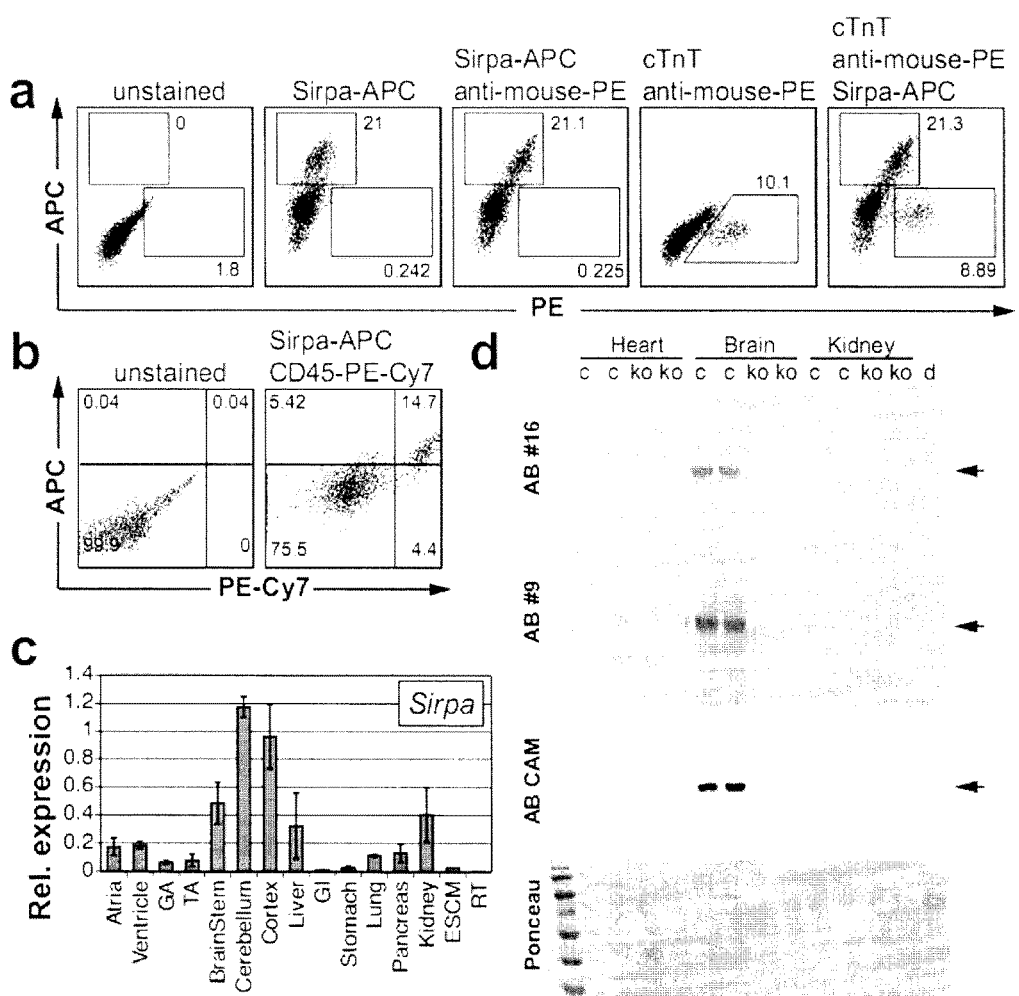

FIG. 14 shows analysis of Sirpa expression in mouse embryonic stem cell-derived cardiomyocytes and adult mouse tissue samples. (a) Flow cytometric analysis of mESC-derived cardiac EB cultures. Cells stained for Sirpa-APC, fixed with 4% PFA and stained with cTnT/antimouse-PE. Sirpa-expressing cells did not co-stain with cTnT-expressing cells, suggesting that cardiomyocytes derived from mES cells do not express Sirpa. (b) Flow cytometric analysis of mESC-derived cardiac EB cultures. Sirpa-positive cells co-stain with CD45-PE-Cy7, suggesting that the Sirpa-positive cells present in these cultures represent hematopoietic cells, which have previously been described to express Sirpa (ref). (c) QPCR analysis of Sirpa in adult mouse tissue samples. TA, tibialis anterior muscle; GA, gastrocnemius muscle; GI, gastrointestinal tract; RT, reverse transcriptase control; ESCM, mouse embryonic stem cell derived cardiomyocytes day7 of differentiation (Kattman et al., 2011). Mouse brain tissue was used as positive control. (d) Western blot analysis of adult heart, brain and kidney tissue from control (c) and Sirpa-deficient mice (ko)(Timms et al., 1999) and mouse ESC-derived cardiomyocytes (d). Sirpa expression was solely detected in the brain tissue of control mice, but not in any of the Sirpa-deficient samples or in the control heart, kidney or mESC-derived samples. Antibodies #16 and #9 (specific for cytoplasmic domain, common to all Sirpa isoforms, AB#16, AB#9) were used as described in Timms et al., 1999. ABCAM: anti-Sirpa antibodies (Abcam, 8120).

Figure 15:
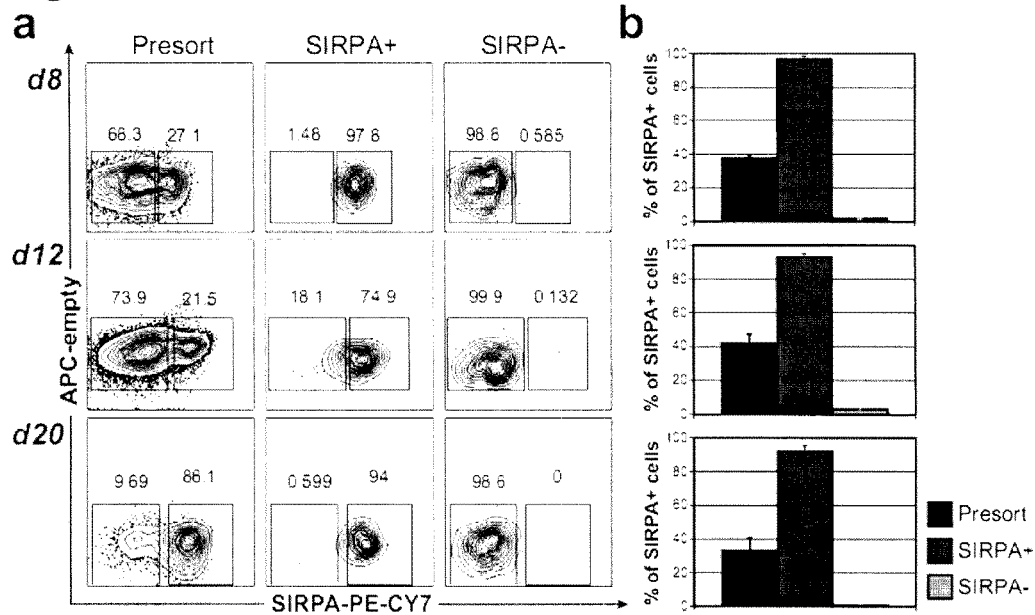

FIG. 15 shows analysis of purity of SIRPA− and SIRPA+ fractions after FACS. (a) Flow cytometric analysis of presort, SIRPA− and SIRPA+ fraction for SIRPA after cell sorting. (b) quantification of SIRPA+ cells in presort, SIRPA− and SIRPA+ fraction after cell sorting, n=3.

Figure 16:
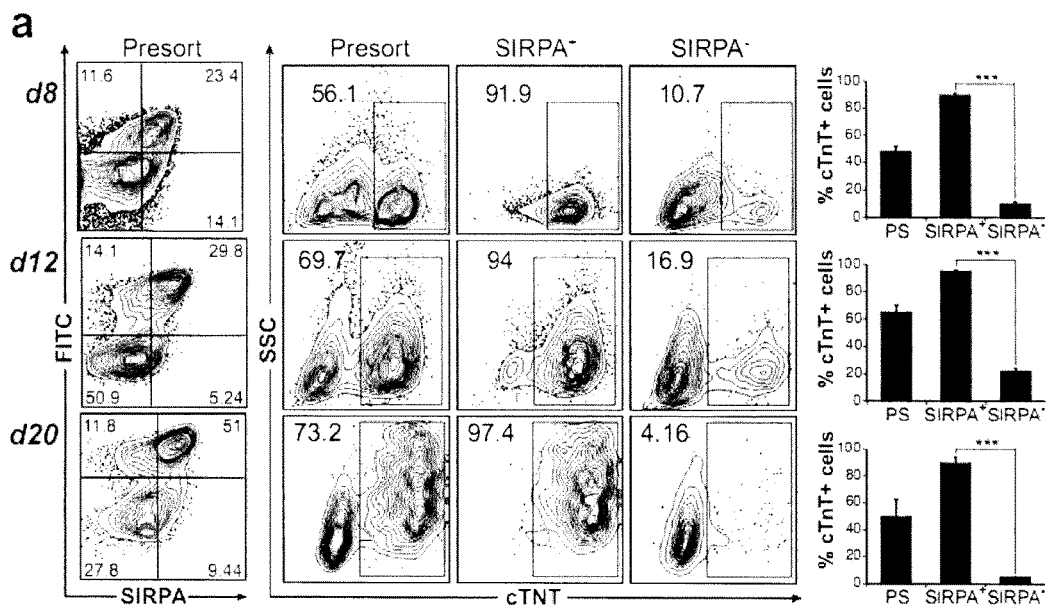
Figure 16:
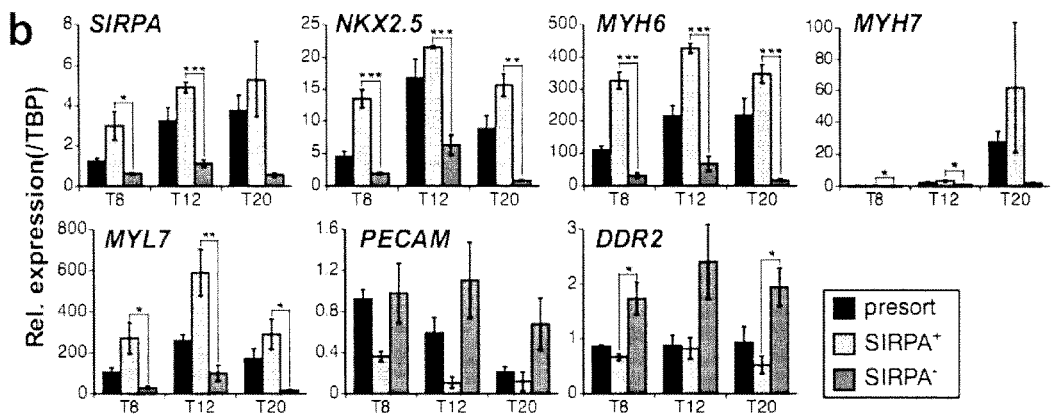

FIG. 16 shows enrichment of cardiomyocytes from hESC-derived cultures by cell sorting based on SIRPA expression. (a) Flow cytometric analysis of SIRPA expression at day (d)8, d12 and d20 of differentiation from NKX2.5-GFP HES3 hESCs. Fluorescent-activated cell sorting (FACS) for SIRPA was performed at d8, d12 and d20 and the presort (PS), SIRPA+ and SIRPA fractions were analysed for cardiac TroponinT (cTnT) expression by intracellular flow cytometry. The frequency of cTnT+ cells at d8, d12 and d20 was significantly higher in the SIRPA+ fraction (day8: 89.8%±1.9, day12: 95.0±1.3, day20: 89.4±4.4), compared to SIRPA− cells (day8: 9.9±1.7, day12: 21.9±2.5, day20: 5.2±0.5), n=3. (b) QPCR analysis of PS, SIRPA+ and SIRPA− cells after cell sorting. Expression of markers specific for the cardiac lineage (NKX2.5, MYH6, MYH7 and MYL7) was significantly higher in the SIRPA+ compared to SIRPA− fraction at all stages analyzed (d8, d12 and d20). Expression of markers for the non-cardiac lineages (PECAM and DDR2) segregated to the SIRPA− fraction and the PS cells, n=3.

Figure 17:
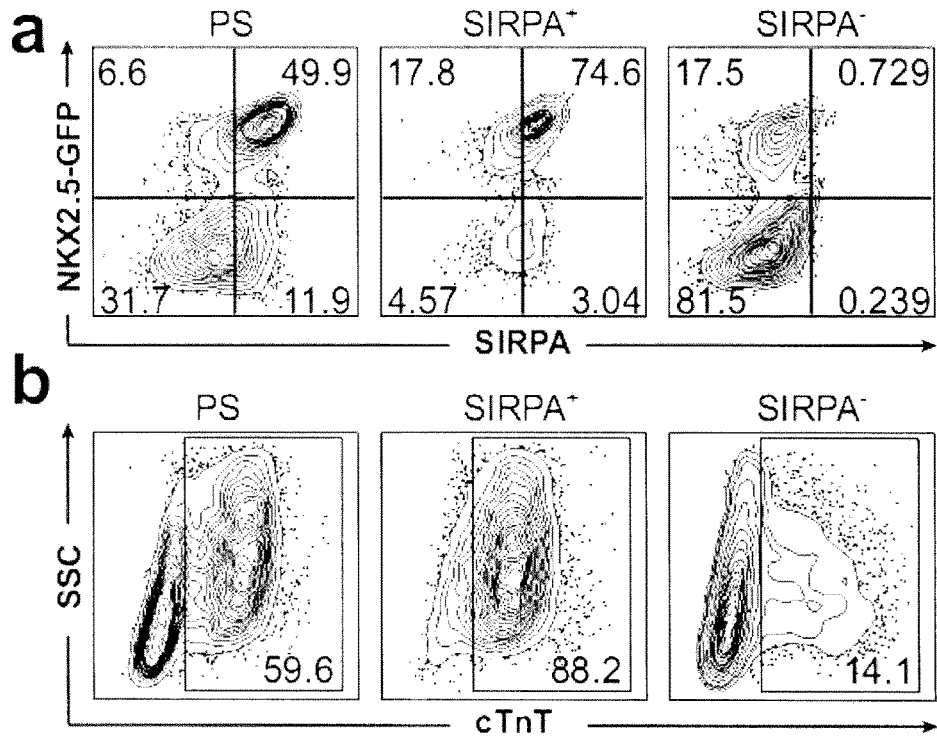

FIG. 17 shows isolation of SIRPA+ cardiomyocytes via bead sorting. (a) Flow cytometric analysis of SIRPA. HES2-derived EBs were sorted using the Miltenyi magnetic bead sorting system and PS, SIRPA+ and SIRPA fractions after sorting were analyzed for SIRPA expression. (b) Intracellular cTnT flow cytometric analysis of PS, SIRPA+ and SIRPA− fractions.

Figure 18:
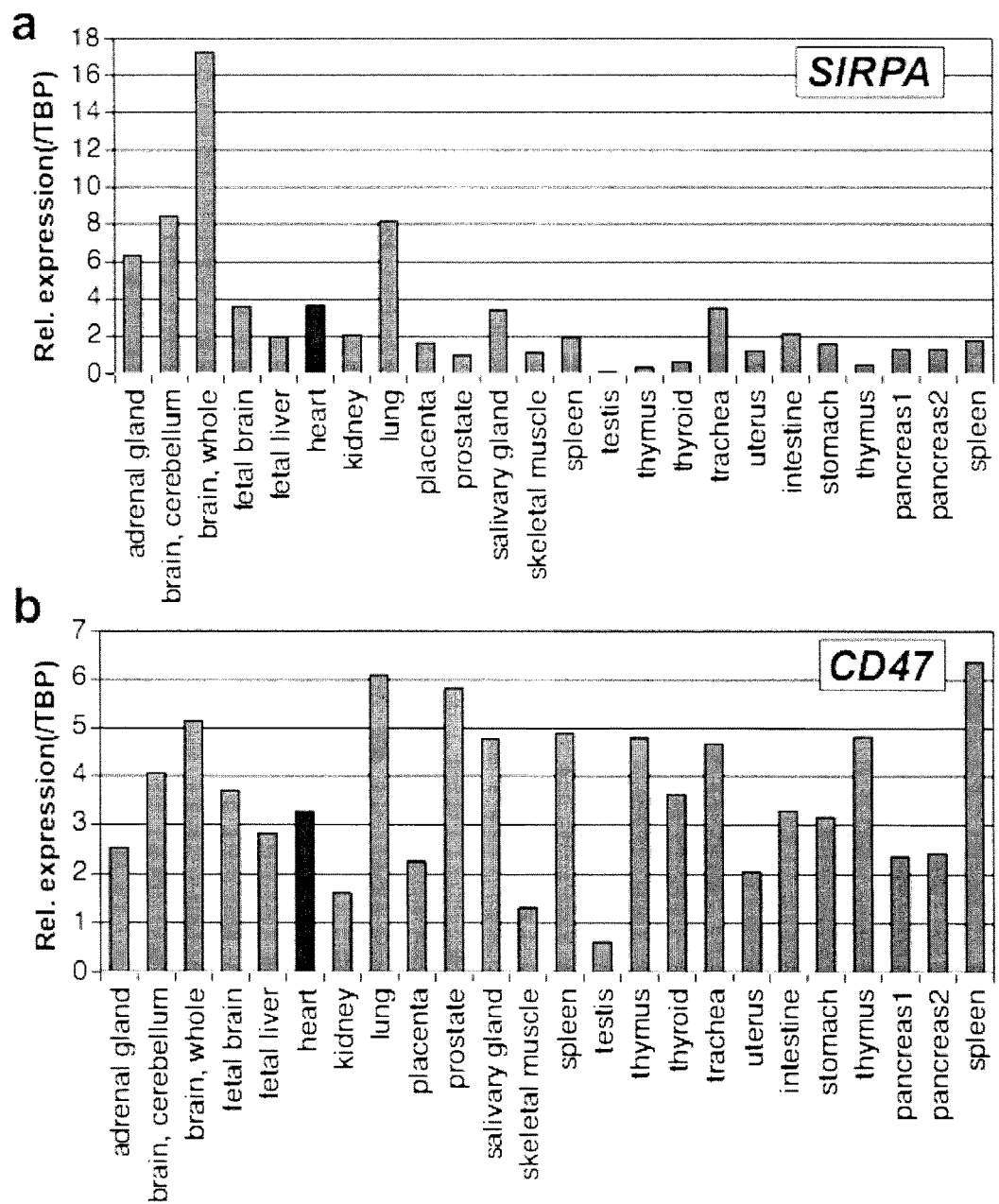

FIG. 18 shows gene expression analysis of human adult tissue. (a) QPCR RT analysis of SIRPA. (b) QPCR RT analysis of CD47.

Figures 19, 20:
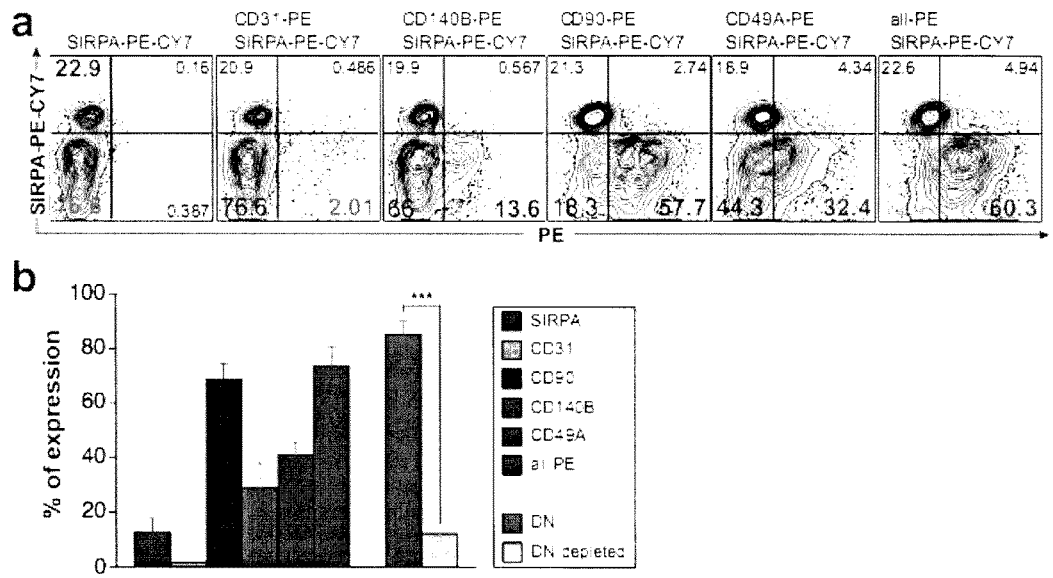

FIG. 19 shows expression of non-myocyte markers in Y2-1-derived differentiation cultures. (a) Flow cytometric analysis of markers specifically expressed on non-myocyte (SIRPA−) cells in day 20 differentiation cultures. (b) Quantification of expression of non-myocyte markers at day 20 of differentiation from Y2-1 iPS cells.

FIG. 20 is a table showing the efficiency of fluorescent-activated cell sorting (FACS) with the SIRPA antibody. (a) Recovery of SIRPA− cells after FACS of EB-derived cells from HES2 at day20 of differentiation, n=8. (b) Recovery of SIRPA+ cells after FACS of EB-derived cells from HES2 at day20 of differentiation, n=9. Total cell #=total cells passed through the flow cytometer; SIRPA− (SIRPA+)#=total SIRPA−(SIRPA+) cells recovered after the sorting procedure; SIRPA−(SIRPA+) %=percentage of SIRPA−(SIRPA+) cells determined by staining with the SIRPA antibody; SIRPA−(SIRPA+) exp cell#=cells number of SIRPA−(SIRPA+) cells expected based on staining with the SIRPA antibody and on total cell number sorted; Eff SIRPA−(SIRPA+)=efficiency of SIRPA−(SIRPA+) cell recovery: SIRPA−(SIRPA+) cell#/SIRPA−(SIRPA+) exp cell#; Eff SIRPA−(SIRPA+)=efficiency of SIRPA−(SIRPA+) cell recovery in percentage.

FIG. 21 is a table showing the efficiency of fluorescent-activated cell sorting (FACS) with the nonmyocyte markers. (a) Recovery of LIN− cells after FACS of EB-derived cells from HES2 at day20 of differentiation, n=6. (b) Recovery of LIN+ cells after FACS of EB-derived cells from HES2 at day20 of differentiation, n=6. Total cell #=total cells passed through the flow cytometer; LIN−(LIN+)#=total LIN−(LIN+) cells recovered after the sorting procedure; LIN−(LIN+) %=percentage of LIN−(LIN+) cells determined by staining with the LIN antibodies; LIN−(LIN+) exp cell#=cells number of LIN−(LIN+) cells expected based on staining with the LIN antibodies and on total cell number sorted; Eff LIN−(LIN+)=efficiency of LIN−(LIN+) cell recovery: LIN−(LIN+) cell#/LIN−(LIN+) exp cell#; Eff LIN−(LIN+)=efficiency of LIN−(LIN+) cell recovery in percentage.

DETAILED DESCRIPTION

There is described herein the use of a high throughput flow cytometry screen to identify cell surface markers specific for human cardiomyocytes. Here we report that the cell surface receptor SIRPA is expressed on hPSC-derived cardiomyocytes as well as on human fetal cardiomyocytes. Using cell sorting with an antibody against SIRPA we demonstrate that it is possible to isolate populations consisting of up to 98% cardiomyocytes from hPSC differentiation cultures.

Cell surface antigen, SIRPA (also known as CD172a, BIT, SHPS1), can be found specifically and exclusively on cardiac progenitor cells and on troponin T-positive cardiomyocyte cells generated from human pluripotent stem cells (hPSCs) under appropriate differentiation conditions.

Prior to the present application, there was no indication or evidence in the art that SIRPA is expressed on developing mouse or human cardiovascular cells. RNA expression of human SIRPA has been found in different parts of the brain as well as in blood and at low levels in the lung. However, SIRPA RNA expression has not been found in the heart (http://biogps.gnf.org). SIRPA protein expression has been detected in the brain, in blood and lymphoid tissues and in the colon, and at moderate to weak levels in placenta, pancreas, spleen, bladder and stomach (http://www.proteinatlas.org/). However, no protein expression has been reported for the adult human heart. As such, the discovery that SIRPA is expressed in hPSC-derived cardiac progenitor cells and cardiomyocyte cells is both novel and surprising.

In one example, the use of a SIRPA binding moiety, such as a SIRPA antibody, provides a simple and novel method to identify, monitor and isolate cardiomyocyte cells and their progenitor cells from populations derived from human embryonic stem cells and induced pluripotent stem cells. Cell isolation is easy and efficient, yielding populations, in one embodiment, consisting of greater than 90% cardiomyocyte cells that remain viable and can be used for the applications disclosed herein.

SIRPA was identified as a potential cardiac marker in a screen of over 350 commercially available antibodies supplied by the Ontario Institute for Cancer Research Antibody Core Facility. The antibodies were screened against hESC-derived populations representing different stages of cardiac development generated by the directed differentiation of the hESCs using a previously published protocol (Yang et al., 2008).[3] Antibodies that stained cell populations of similar size to the cardiomyocyte population in the differentiation cultures (as defined by cardiac troponin T (cTnT) staining) were investigated further and used for cell sorting. Of the 350 surface antibodies, one antibody, SIRPA, specifically and exclusively stained the hESC-derived cardiomyocyte population.

Cells isolated based on SIRPA expression represent a novel source of highly enriched pluripotent stem cell-derived cardiomyocyte progenitor cells (e.g. at the onset of Nkx2.5 expression but before cell contraction and expression of the cardiac-specific structural proteins) and cardiomyocyte cells for various applications, including but not limited to the establishment of patient-specific disease models as well as genetic, epigenetic and proteomic analyses of cardiac progenitor cells and cardiomyocyte cells from normal and patient-specific pluripotent stem cells.

The specific expression of SIRPA on cardiac cells and their precursors suggests a function for this receptor and its downstream signalling pathways during cardiac development and differentiation.

SIRPA can also be used as a negative marker for cell sorting experiments to enrich for non-cardiogenic PSC-derived lineages such as including those derived from the somite (progenitor cells of skeletal muscle, bone, and cartilage/chondrocytes).

Therefore, in one aspect, there is provided a method of enriching a population of cells for cardiomyocyte cells and cardiomyocyte progenitor cells comprising providing the population of cells from which cardiomyocyte cells and cardiomyocyte progenitor cells are to be isolated; and isolating from the population, cells expressing SIRPA; wherein the population of cells comprises a population of human pluripotent stem cells induced to differentiate into cardiomyocyte cells and cardiomyocyte progenitor cells.

In one embodiment, the human pluripotent stem cells are embryonic stem cells. In another embodiment, the human pluripotent stem cells are induced pluripotent stem cells.

In some embodiments, the human pluripotent stem cells are exposed to an amount of at least one inducing agent effective to induce cell differentiation.

In a preferable embodiment, the at least one inducing agent comprises a cytokine. The at least one inducing agent may comprise activin A, preferably at a concentration of up to 40 ng/ml, further preferably at a concentration of about 6 ng/ml or about 30 ng/ml. the at least one inducing agent may also independently comprise bone morphogenetic protein 4, preferably at a concentration of up to 40 ng/ml, further preferably at a concentration of about 10 ng/ml.

In some embodiments, the human pluripotent stem cells are further exposed to a bone morphogenetic protein inhibitor, preferably selected from the group consisting of Dorsomorphin, Noggin and soluble bone morphogenetic protein receptors.

In some embodiments, the human pluripotent stem cells are further exposed to at least one of VEGF, DKK and bFGF In some embodiments, the human pluripotent stem cells are exposed to the inducing agent for between about 1 and about 5 days, preferably about 3 days.

In some embodiments, the time between the initiation of induction of the human pluripotent stem cells and isolating the cells expressing SIRPA is between about five days and about forty-five days, preferably between about 8 and about 25 days.

In some embodiments, the cells expressing SIRPA are isolated after the onset of SIRPA expression by the cells, which appears around the time of onset of Nkx2.5 expression by the cells. Preferably, the cells having the SIRPA cell surface antigen are isolated between the time of the onset of Nkx2.5 expression by the cells and the time of the onset of contraction and expression of the cardiac-specific structural proteins by the cells.

In some embodiments, the method further comprises depleting from the population, cells expressing at least one of CD90, CD31, CD140B and CD49A, preferably using a corresponding antibody.

Methods for isolating cells expressing a particular molecule, in this case SIRPA, are known to a person skilled in the art. In some embodiments, the presence of SIRPA is directly used to isolate cells by using a SIRPA-specific ligand, preferably using an anti-SIRPA antibody or antibody fragment, or antibody-like molecule, and further preferably an anti-SIRPA antibody. In some embodiments, the cells are then isolated using magnetic beads and/or flow cytometry. Alternatively, cells expressing SIRPA may be indirectly selected. For example, in some embodiments, the cells in the population comprise a reporter gene operably linked to regulatory control elements of the SIRPA locus whereby the reporter gene is expressed in cells that express SIRPA and the step of isolating the cells expressing SIRPA comprises isolating cells expressing the reporter gene. In one preferable embodiment, the reporter gene confers resistance to a cytotoxic agent. In another preferable embodiment, the reporter gene is a cell surface tag.

In some embodiments, the enriched population of cells comprises at least 60%, preferably at least 90%, further preferably 98%, cardiomyocyte cells and cardiomyocyte progenitor cells.

In a further aspect, there is provided an enriched population of cardiomyocyte cells and cardiomyocyte progenitor cells obtained using any one of the methods described herein.

In a further aspect, there is provided an isolated population of cells enriched for cardiomyocyte cells and cardiomyocyte progenitor cells, wherein the population of cells comprises at least 60%, preferably at least 90%, further preferably 98%, cardiomyocyte cells and cardiomyocyte progenitor cells.

In a further aspect, there is provided the use of SIRPA for isolating cardiomyocyte cells and cardiomyocyte progenitor cells from a population of cells, wherein the population of cells comprise a population of human pluripotent stem cells induced to differentiate into cardiomyocyte cells and cardiomyocyte progenitor cells.

In a further aspect, there is provided a method of depleting a population of cells for cardiomyocyte cells and cardiomyocyte progenitor cells comprising: providing the population of cells from which cardiomyocyte cells and cardiomyocyte progenitor cells are to be depleted; and depleting from the population, cells expressing SIRPA; wherein the population of cells comprises a population of human pluripotent stem cells induced to differentiate into cardiomyocyte cells, cardiomyocyte progenitor cells, and non-cardiomyocytes.

In a further aspect, there is provided a method of enriching a population of cells for cardiomyocyte cells and cardiomyocyte progenitor cells comprising: providing the population of cells from which cardiomyocyte cells and cardiomyocyte progenitor cells are to be isolated; and depleting from the population, cells expressing at least one of CD90, CD31, CD140B and CD49A; wherein the population of cells comprise a population of human pluripotent stem cells induced to differentiate into cardiomyocyte cells, and cardiomyocyte progenitor cells, and non-cardiomyocytes.

The term "enriching", as used in the context of the present invention, includes any isolation or sorting process that increases the relative abundance of a desired cell type, or cell types, in a population of cells.

As used herein, the term "cardiomyocyte cells" refers to the cells that comprise cardiac muscle.

The term "cardiomyocyte progenitor cells" means progenitor cells derived from human pluripotent stem cells that have the capacity to differentiate into cardiomyocyte cells.

As used herein, the process of "isolating cells" refers to any method known to those skilled in the art for sorting cells including, but not limited to, flow cytometry, fluorescence activated cell sorting, magnetic separation using antibody-coated magnetic beads, affinity chromatography, and the exploitation of differences in physical properties (e.g., density gradient centrifugation).

"Embryonic stem cells" ("ESC") are pluripotent stem cells that are derived from early-stage embryos.

"Induced pluripotent stem cells" ("iPSC"), as used in the context of the present invention, is a type of pluripotent stem cell that has been artificially derived from a non-pluripotent cell by inducing the expression of specific genes.

The term, "cell surface antigen", refers to antigens on surfaces of cells that are capable of being recognized by the immune system and binding specifically to an antibody.

As used herein, the phrase "induced to differentiate" refers to any method known in the art used to initiate the differentiation of human pluripotent stem cells into specialized cell types. These methods may include exposure of the human pluripotent stem cells to an inducing agent.

As used herein, the term "inducing agent" refers to any agent capable of initiating differentiation of hPSCs into specialized cell types, including cardiomyocyte cells and cardiomyocyte progenitor cells. Inducing agent therefore includes cytokines, including but not limited to activin A, bone morphogenetic protein 4 (BMP4), basic fibroblast growth factor (bFGF, also known as FGF2), vascular endothelial growth factor (VEGF, also known as VEGFA), dickkopf homolog 1 (DKK1), and combinations therefrom.

Methods for inducing human pluripotent stem cells to differentiate into cardiomyocyte cells and cardiomyocyte progenitor cells are known to a person skilled in the art (for e.g., see Yang et al.[3], and Laflamme et al.[19]). In some embodiments, induction conditions (e.g. concentrations of the inducing agents and timing of their use) can be optimized by measuring SIRPA concentration in the resulting enriched population.

The ability to generate cells of the cardiac lineage from human pluripotent stem cells hPSCs (including embryonic stem cells; hESCs and induced pluripotent stem cells; hiPSCs) provides a novel and unlimited supply of human cardiomyocyte cells that will be useful for: 1) predictive drug toxicology and drug discovery, 2) transplantation for the treatment of cardiovascular disease and 3) modeling cardiovascular development and disease in vitro.

The following examples are illustrative of various aspects of the invention, and do not limit the broad aspects of the invention as disclosed herein.

EXAMPLES

Materials and Methods
HPSC Maintenance and Differentiation

Figure 1:
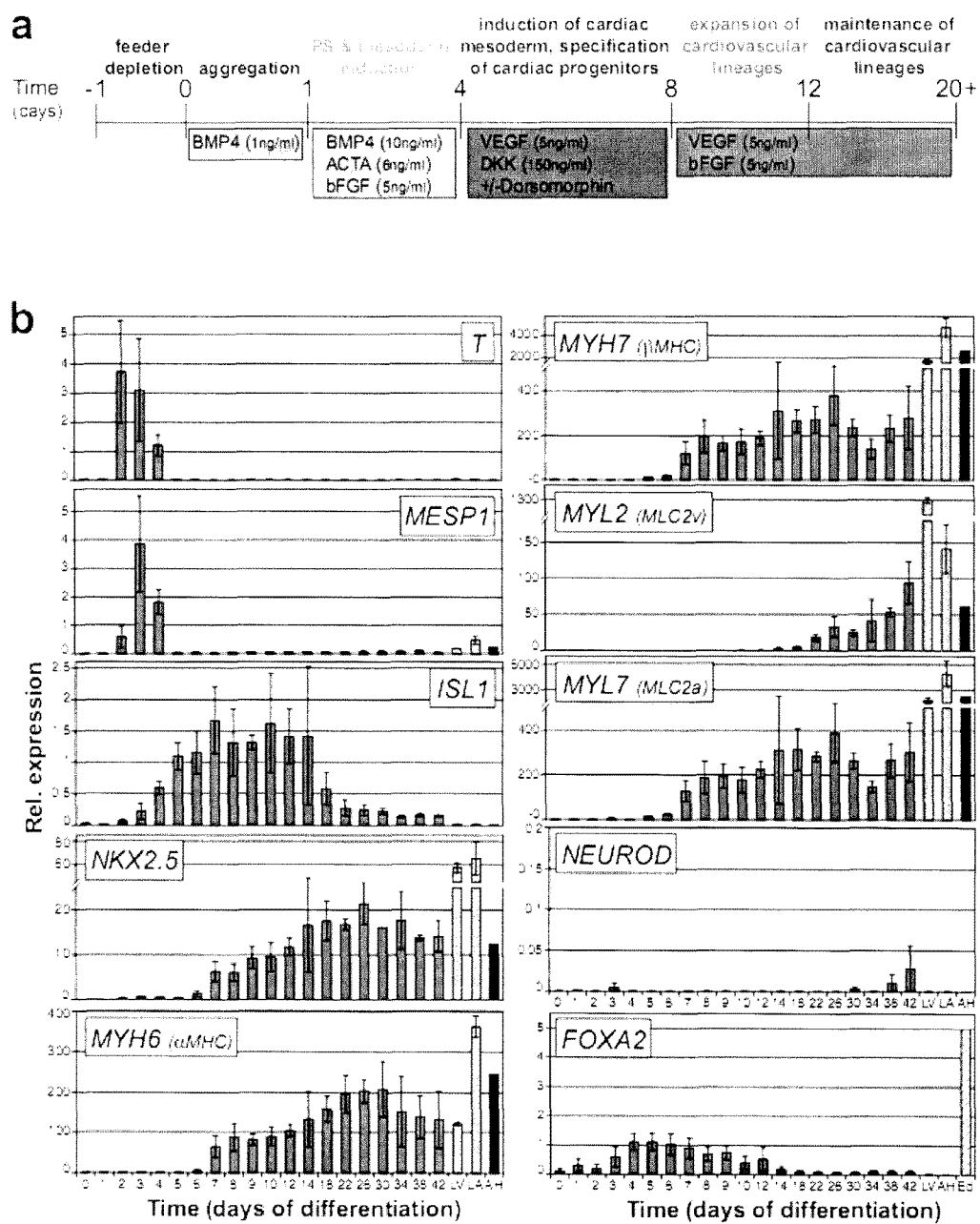
FIG. 1 shows specification of the cardiovascular lineage from hESCs. (a) Outline of the protocol used to differentiate hESCs to the cardiac lineage (modified from Yang et al., 2008). (b) Quantitative PCR (QPCR) analysis of BRACHURY (T), MESP1, ISLET1 (ISL1), NKX2-5, MYH6 (αMHC), MYH7 (βMHC), MYL2 (MLC2v), MYL7 (MLC2a), NEUROD1 and FOXA2 in HES2-derived embryoid bodies (EBs) at different stages during differentiation. Day 0, hES cells; LV, human fetal left ventricle; LA, human fetal left atria; AH, human adult heart, Ed, hESC-derived endoderm[13]. Bars represent mean±standard error of the mean, n=3.

HPSCs were maintained as described[26]. Embryoid bodies (EBs) were differentiated to the cardiovascular lineage as previously described[2,3] (FIG. 1a). In brief: EBs were generated on day0 (d0) and BMP4 (1 ng/ml) was added for the first day of differentiation (d0-d1). At d1, EBs were harvested and resuspended in induction medium (basic fibroblast growth factor (bFGF; 2.5 ng/ml), Activin A (6 ng/ml) and BMP-4 (10 ng/ml)). The medium was changed on d4 and was supplemented with vascular endothelial growth factor (VEGF; 10 ng/ml) and DKK (150 ng/ml). Media was changed again on d8 and was supplemented with VEGF (20 ng/ml) and bFGF (10 ng/ml). EBs were cultured in StemPro-34 (Invitrogen) throughout the experiment. Cultures were maintained in a 5% $CO_2$, 5% $O_2$, 90% $N_2$ environment from d0-d12 and were then transferred into a 5% $CO_2$/air environment for the remainder of the culture period.

NKX2-5-GFP hESCs were generated by targeting sequences encoding GFP to the NKX2-5 locus of HES3 cells using previously described protocols[27] (D.E., A.G.E. and E.G.S., manuscript submitted).

Work involving human tissue collection and analysis was carried out in accordance with and approved through the Human Ethics Committee at the University Health Network.

Flow Cytometry and Cell Sorting

Dissociation procedure for day5 to day12 EBs: EBs generated from hPSC differentiation experiments were dissociated with 0.25% trypsin/EDTA. Dissociation procedure for day13 and older EBs and human fetal tissue: EBs generated from hPSC differentiation cultures were incubated in collagenase type II (1 mg/ml; Worthington, LS004176) in Hanks solution (NaCl 136 mM, NaHCO3 4.16 mM, NaPO4 0.34 mM, KCl 5.36 mM, KH2PO4 0.44 mM, Dextrose 5.55 mM, Hepes 5 mM) over night at room temperature with gentle shaking[28]. The following day, the equivalent amount of dissociation solution (in Hanks solution: taurin, 10 mM, EGTA 0.1 mM, BSA 1 mg/ml, collagenase type II 1 mg/ml) was added to the cell suspension and the EBs were pipetted gently for complete dissociation. Cells were centrifuged (1000 rpm, 5 min) and filtered. For EBs past day 40 of differentiation, additional treatment with 0.25% trypsin/EDTA may be required in order to obtain complete dissociation into single cells.

Cells were stained at a concentration of $2.5\times10^6$ cells/ml with anti-KDR—allophycocyanin (R&D Systems; 1:10) and anti-PDGFRA—phycoerythrin (R&D Systems; 1:20), anti-SIRPA– IgG-phycoerythrin-Cy7 (clone SE5A5; BioLegends; 1:500)[10,29], anti-SIRPA– IgG-biotin (clone SE5A5; BioLegends; 1:500)[10], anti-cardiac isoform of Troponin T (cTNT)(clone 13-11; NeoMarkers; 1:400), goat anti-mouse IgG—allophycocyanin (BD; 1:200), Streptavidin—allophycocyanin (BD; 1:200), anti-IgG1κ-phycoerythrin-Cy7 (clone MOPC-21; BioLegends; 1:500), anti-IgG1κ-biotin (clone MOPC-21; BioLegends; 1:500).

For cell surface markers, staining was carried out in PBS with 10% FCS. For intracellular proteins, staining was carried out on cells fixed with 4% paraformaldehyde (Electron Microscopy Sciences, Hatfield, Pa., USA) in PBS and stainings were performed in PBS with 10% FCS and 0.5% saponin (Sigma). Stained cells were analyzed using an LSRII flow cytometer (BD). For fluorescent activated cell sorting, the cells were sorted at a concentration of $10^6$ cells/ml in IMDM/6% FCS using a FACSAriaTMII (BD) cell sorter (SickKids-UHN Flow Cytometry Facility, Toronto, ON, Canada). In order to prevent cell death due to pressure and sheer stress, all sorts were performed with a 100 micron nozzle. For magnetic bead sorting, the Miltenyi MACS bead sorting system was used and the experiments were carried out according to the manufacturer's guidelines and the sorting conditions for dim markers. For the high throughput flow cytometry analysis the BD high throughput sampler (HTS) for the LSRII was used according to the manufacturers guidelines. Data were analyzed using FlowJo software (Treestar, Ashland, Oreg., USA).

Immunostaining

Immunostaining was performed as previously described[13] using the following primary antibodies: rabbit anti-cardiac Troponin I (Abcam; 1:100), mouse anti-SIRPA (BioLegends; 1:100). Secondary antibodies used were: goat anti-mouse IgGCy3 (Jackson ImmunoResearch; 1:400), donkey anti-mouse IgG-Alexa 488 (Invitrogen; 1:400). DAPI was used to counterstain nuclei. Mito Tracker Red (Invitrogen) was used to stain mitochondria. The stained cells were visualized using a fluorescence microscope (Leica CTR6000) and images captured using the Leica Application Suite software.

Quantitative Real-Time PCR

Total RNA was prepared with the RNAqueous-Micro Kit (Ambion) and treated with RNase-free DNase (Ambion). 500 ng to 1 µg of RNA was reverse transcribed into cDNA using random hexamers and Oligo (dT) with Superscript III Reverse Transcriptase (Invitrogen). QPCR was performed on a MasterCycler EP RealPlex (Eppendorf) using QuantiFast SYBR Green PCR Kit (Qiagen) as described previously[13]. Expression levels were normalized to the housekeeping gene TATA box binding protein (TBP). In addition to TBP for normalization across samples, genomic DNA was used as a DNA standard. The copy number of the target gene present in the genomic DNA can be directly calculated (Human genome size: $2.7\times10^9$ bp (=$1.78\times10^{12}$ daltons), corresponds to $6.022\times10^{23}$ copies of a single copy gene; 1 ug of genomic DNA corresponds to $3.4\times10^5$ copies of a single copy gene). The Y-axis of RT-qPCR graphs represents copy numbers of the gene of interest divided by copy numbers of TBP, and therefore represents an arbitrary but absolute unit, that can be compared between experiments.

Total human adult heart RNA was purchased from Ambion and a total human RNA master panel was purchased from Clontech.

Results & Discussion

Identification of Novel Markers Expressed on hESC-Derived Cardiomyocytes

Figure 8:
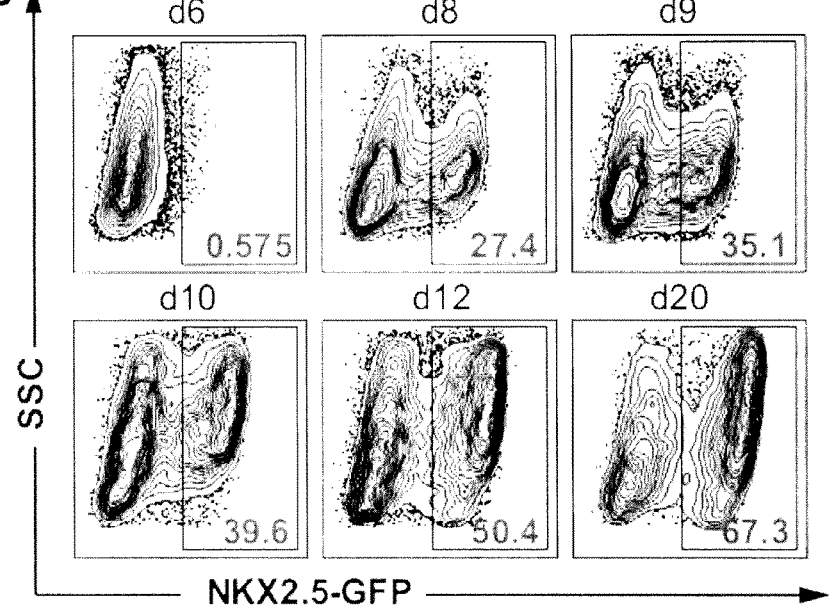
FIG. 8 shows differentiation kinetics of the NKX2.5-GFP HES3 hESC line. Flow cytometric analysis of EBs derived from the NKX2.5-GFP hESC line at various times during differentiation. GFP expression is first detected at day8 of differentiation and increases over time with maximum expression at day20.

When induced with appropriate concentrations of Activin A and BMP4 (FIG. 1a), the HES2 hESC line efficiently and reproducibly differentiates to generate cardiovascular lineage cells[2,3]. Kinetic analyses of the differentiation cultures revealed a step-wise developmental progression from a primitive streak-like population defined by BRACHYURY (T) expression (days 2-4) to the development of the early mesoderm (MESP1; days 3-4) and the emergence of NKX2-5 and ISLET1 (ISL1) positive cardiac precursors (days 4-8). Contracting cardiomyocytes were first detected between days 9 and 12 of differentiation, coincident with the up-regulation of MYH6 (αMHC), MYH7 (βMHC) and MYL7 (MLC2a) and later MYL2 (MLC2v) expression (FIG. 1b). The levels of expression of some of the cardiac specific genes in the hESC-derived populations were considerably lower than the levels found in fetal and adult heart tissue. Low levels of NEUROD1 and FOXA2 expression indicate that the cultures were not contaminated with substantial numbers of neuroectoderm or endoderm-derived cells. To be able to monitor cardiomyocyte development in real time, we applied the above protocol to an NKX2-5-GFP reporter hESC line that contains the EGFP cDNA inserted into the NKX2-5 locus of HES3 hESCs (Elliott et al., manuscript submitted). The first NKX2-5-GFP+ cells developed between days 7 and 8 of differentiation. The size of the NKX2-5-GFP+ population increased with time, reaching a maximum between days 12-20 (FIG. 8). Analysis of NKX2-5-GFP ESC-derived embryoid bodies (EBs) under epifluorescence confirmed nuclear GFP expression in the majority of the cells. The kinetics of NKX2-5-GFP expression closely parallels the onset of NKX2-5 expression in the HES2 cultures, indicating that cardiac specification from both hESC lines takes place between days 6 and 8 of differentiation (FIG. 1b, FIG. 8). The high proportion of NKX2-5-GFP+ cells in day 20 cultures demonstrates that the differentiation protocol used efficiently promotes the generation of cardiomyocytes from this hESC line.

Figure 2:
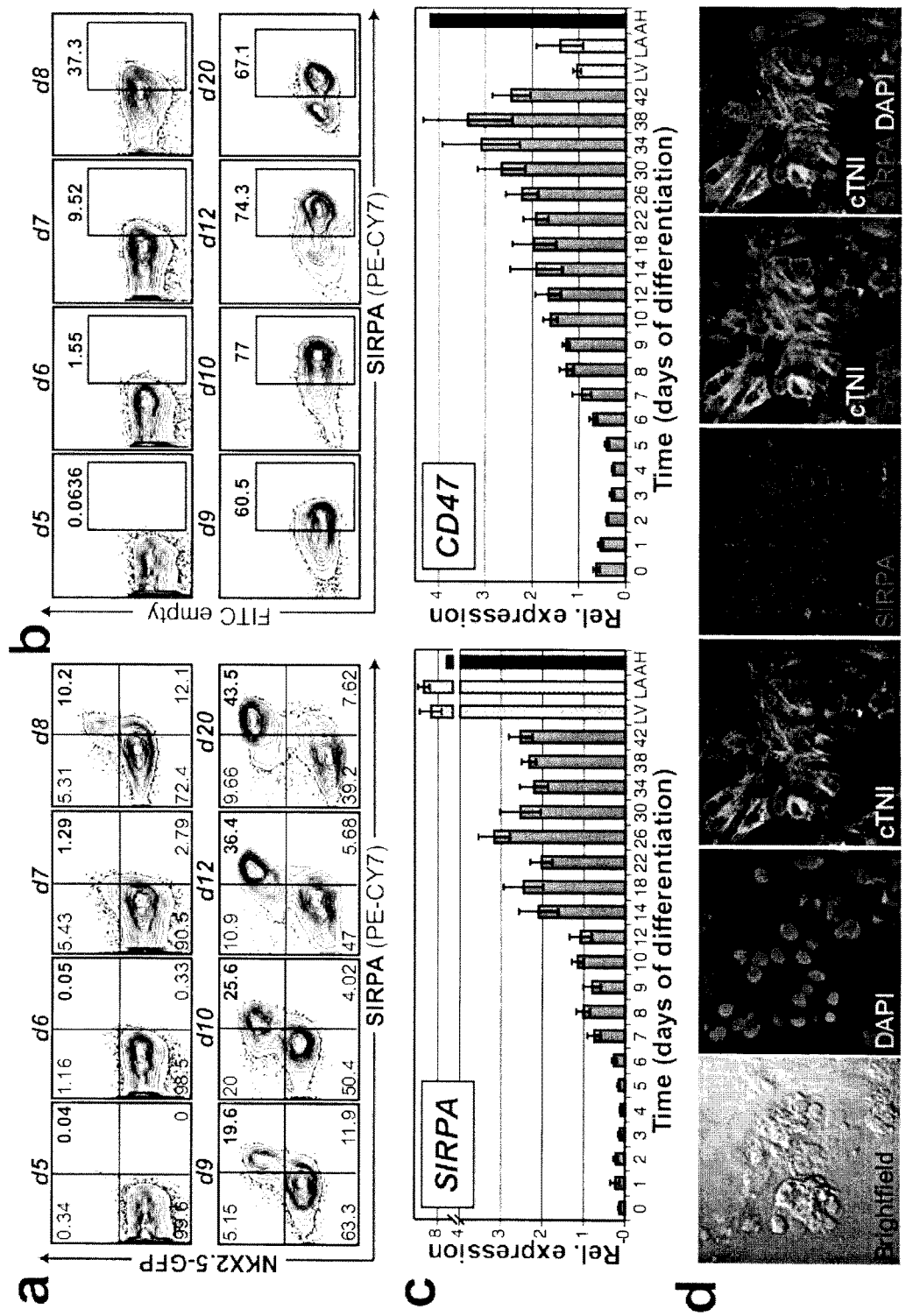
FIG. 2 shows expression of the cell surface receptor SIRPA during hESC differentiation. (a) Flow cytometric analysis of SIRPA (SIRPA) on EBs derived from NKX2-5-GFP hESCs. (b) Expression of SIRPA on HES2-derived EB populations at the indicated times. (c) RT-qPCR analysis of expression of SIRPA and its ligand CD47 in HES2-derived EBs at different times of differentiation. Day 0, ES cells; LV, human fetal left ventricle; LA, human fetal left atrial; AH, human adult heart. Bars represent mean±standard error of the mean, n=4. (d) Immunostaining for SIRPA and cardiac Troponin I (cTNI) on cardiac monolayer cultures. Monolayers were generated from d20 HES2-derived EBs.
Figure 9:
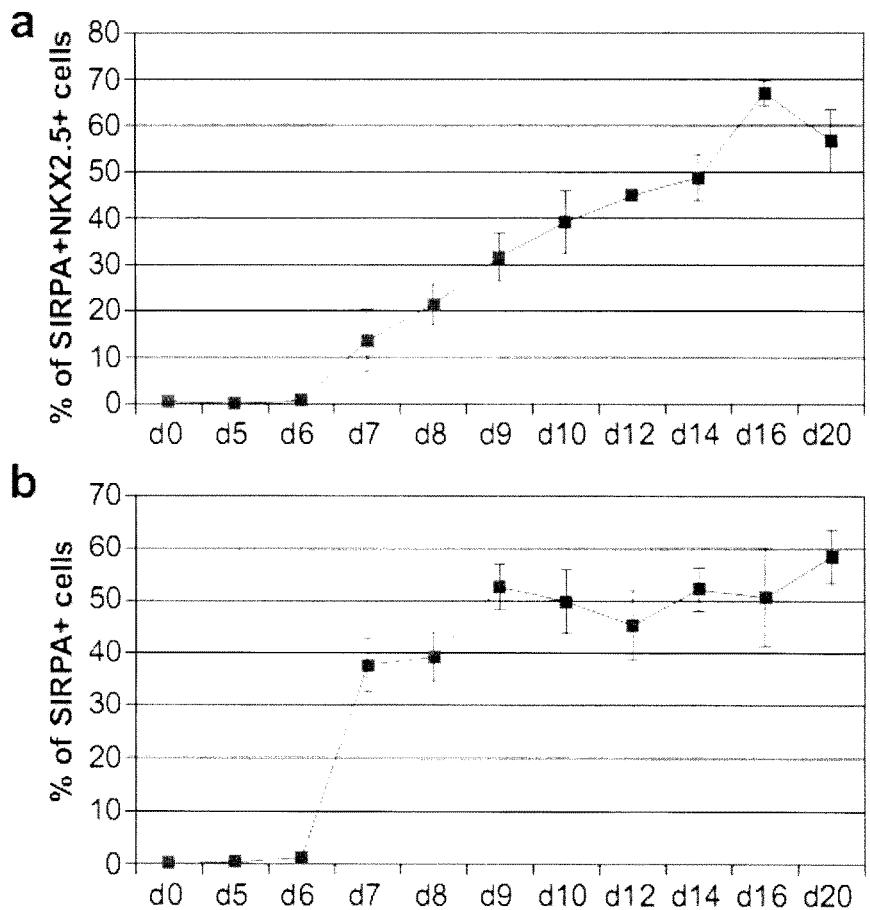
FIG. 9 shows SIRPA expression kinetics of the NKX2.5-GFP HES3 and the HES2 hESC lines. (a) Analysis and quantification of SIRPA+/NKX2.5-GFP+ cells by flow cytometric analysis. EBs derived from the NKX2.5-GFP hESC line were analyzed at various times during differentiation, n=5. (b) Analysis and quantification of SIRPA+ cells by flow cytometric analysis. EBs derived from the HES2 hESC line were analyzed at various times during differentiation, n=8. d0=undifferentiated ES cells, d5-d20=differentiated EBs at day5-day20.
Figure 10:
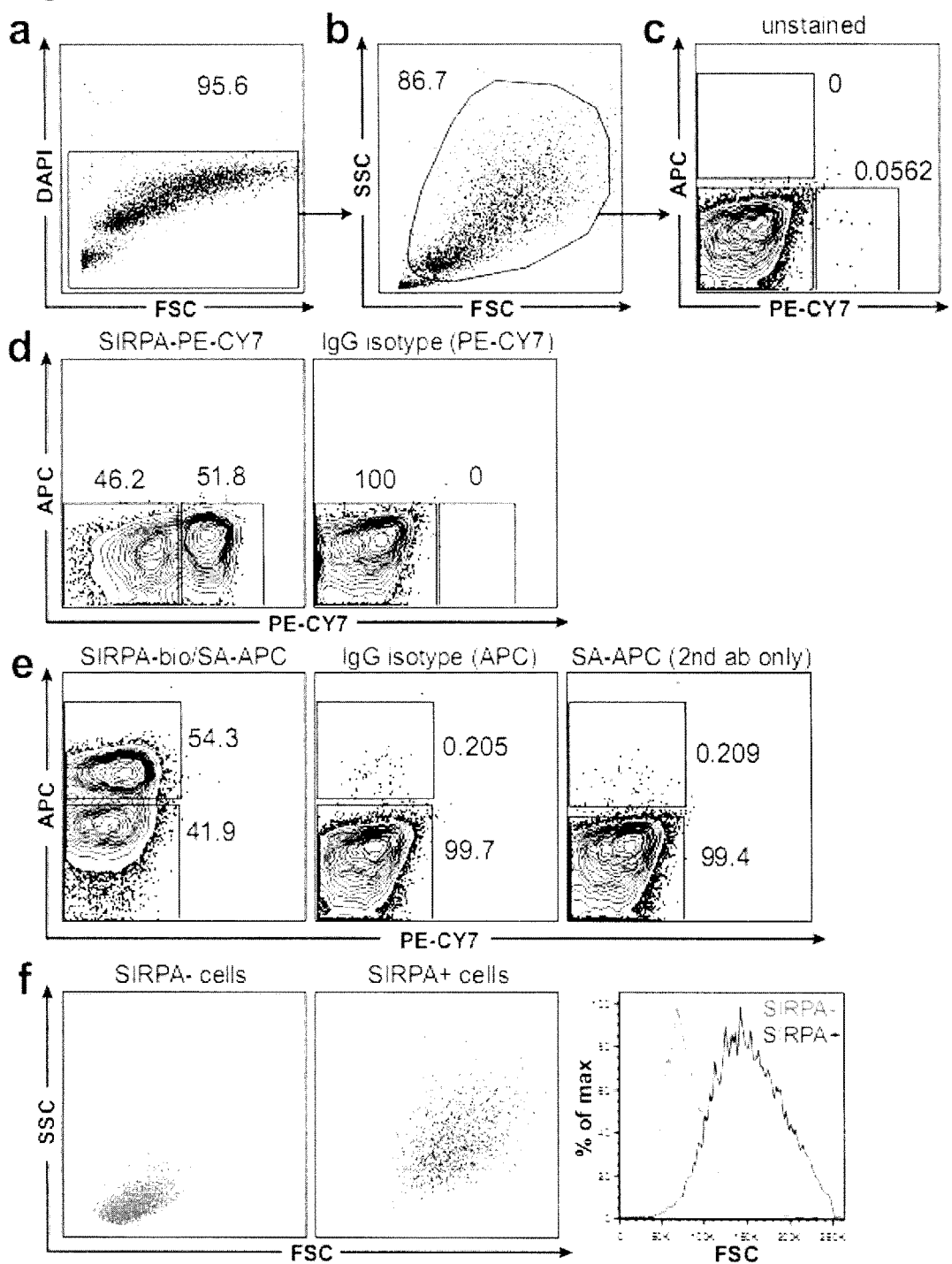
FIG. 10 shows flow cytometry analysis strategy and staining controls. (a) Flow cytometric analysis of day20 EB-derived cells. All cells were stained with the viability dye DAPI and only DAPI-negative cells (=viable cells) were analyzed for each experiment. (b) Viable single cells were further determined by FSC/SSC (cell size and granularity) in order to exclude debris and doublets or cell clumps. (c)

To determine if the above developmental stages can be distinguished by cell surface markers, we carried out a screen of 370 known antibodies (http://data.microarrays.ca/AntibodyWeb) using day 8, 12, and 20 populations generated from the GFP-NKX2-5 cell line. The initial screen focused on identifying antibodies that recognized antigens present on the NKX2-5-GFP$^+$ population. From this screen, we identified signal-regulatory protein alpha (SIRPA, also known as SHPS-1, SIRPA) as a potential cardiac-specific marker, as the anti-SIRPA antibody[10] stained the majority of the NKX2-5-GFP$^+$ cells and almost none of the negative cells (FIG. 2a). From the panel of antibodies analyzed, SIRPA was the only one that displayed this cardiomyocyte specific expression pattern. SIRPA was first detected on the emerging GFP-NKX2-5$^+$ cells at day 8 of differentiation, a population considered to represent the cardiac precursor stage of development. Expression was maintained on GFP-NKX2-5$^+$ population throughout the 20-day time course of the experiment (FIG. 2a, FIG. 9a). No SIRPA$^+$ cells were detected in undifferentiated hESC populations or in the day 5 cardiac mesoderm population characterized by co-expression of KDR and PDGFRA (FIG. 2a and data not shown)[2]. Analyses of EBs generated from the non-genetically modified HES2 line revealed a similar staining pattern with the anti-SIRPA antibody. SIRPA$^+$ cells were first detected at days 7-8 of differentiation and the percentage of positive cells increased significantly over the next 2-4 days (FIG. 2b, FIG. 9b). Both the directly conjugated (SIRPA-PE-CY7) and the biotinylated (SIRPA-bio) antibodies stained similar portions of the day 20 EB population (FIG. 10a-e). Interestingly, the SIRPA$^+$ cells detected in day 20 EBs appear to be substantially larger than those found in the SIRPA$^-$ population (FIG. 10f), suggesting that cell size of these populations can be assessed by flow cytometry. To confirm the specificity of the SIRPA antibody, we carried out Western Blot analyses and immunoprecipitation followed by Western Blot analysis (FIG. 11). These experiments demonstrated the presence of SIRPA protein in 3 independent day EB-derived populations, but not in undifferentiated hESCs (FIG. 11a). Immunoprecipitation analyses revealed a band the size of that previously described for the SIRPA protein (FIG. 11b)[11].

Co-staining of SIRPA and cTNT by flow cytometry displayed clear co-expression of the two markers (FIG. 12a/b), indicating that SIRPA was specifically expressed on the cardiomyocyte lineage in differentiated populations generated from the non modified HES2 cell line.

RT-qPCR analyses revealed an expression pattern for SIRPA that closely mirrored the flow cytometry antibody staining profile, with an up-regulation of SIRPA mRNA between days 6 and 8 of differentiation, followed by persistence of expression over the 42-day time course. Expression of CD47, the ligand for SIRPA, paralleled that observed for SIRPA (FIG. 2c). Flow cytometric analysis of CD47 reflected the gene expression pattern, showing low levels of staining on undifferentiated ES cells and on day 5 differentiation cultures, followed by broad staining on the entire population at days 8 and 20 (data not shown).

Immunofluorescence analysis of monolayer cultures derived from day 20 EBs revealed SIRPA surface expression exclusively on cardiomyocytes, as characterized by co-expression with cardiac TroponinI (cTNI)(FIG. 2d) The respective controls (IgG and secondary antibody only) did not show any signal (data not shown). Collectively, these kinetic studies show that expression of SIRPA uniquely marks the cardiac lineage in hESC differentiation cultures, beginning with the emergence of NKX2-5$^+$ precursor cells and persisting through the development and expansion of contracting populations.

Hattori et al recently demonstrated it was possible to isolate cardiomyocytes based on mitochondria content, as measured by retention of a mito tracker dye[9]. Comparison of mito tracker dye labeling with SIRPA staining indicated that both procedures mark the same cardiomyocyte population in day 20 EBs (FIG. 13c). The dye retention approach was, however, less useful in tracking the onset of cardiovascular development, as it marked a less distinct population at day 12 of differentiation and almost no cells at day 8 (FIG. 13a/b). In contrast, a substantial SIRPA$^+$ population could be clearly resolved at both these time points indicating that this surface marker allows one to monitor and isolate cells from different stages of cardiac development, whereas labeling with the mito tracker dye can only be used on populations containing relatively mature cardiomyocytes.

In contrast to the human cells, Sirpa was not detected on mouse ESC-derived cardiomyocytes by antibody staining (FIG. 14a). Sirpa$^+$ populations in the culture were cardiac Troponin T (cTnT) negative and CD45 positive, indicating that they represent hematopoietic cells (FIG. 14a/b). Gene expression analyses confirmed the flow cytometric data, and showed only low levels of Sirpa mRNA in the mESC-derived cardiomyocytes as well as in adult mouse atrial and ventricular tissues, compared to high expression in the brain (FIG. 14c). Expression of the only other known Sirp family member in the mouse, Sirpb, could not be detected in any of these tissues by qPCR (data not shown). Western blot analysis of control and Sirpa-deficient mouse tissue confirmed high Sirpa expression in the brain of control mice, but not in any of the tissues derived from Sirpa-deficient mice (FIG. 14d). Most importantly, no Sirpa expression was detected in the heart, kidney or mESC-derived cardiomyocytes from control mice.

Differences in SIRPA function and protein homology for mouse and human have been described previously for the interaction of macrophages and red blood cells[12].

Purification of Cardiomyocytes from hESC-Derived Populations

Figure 3:
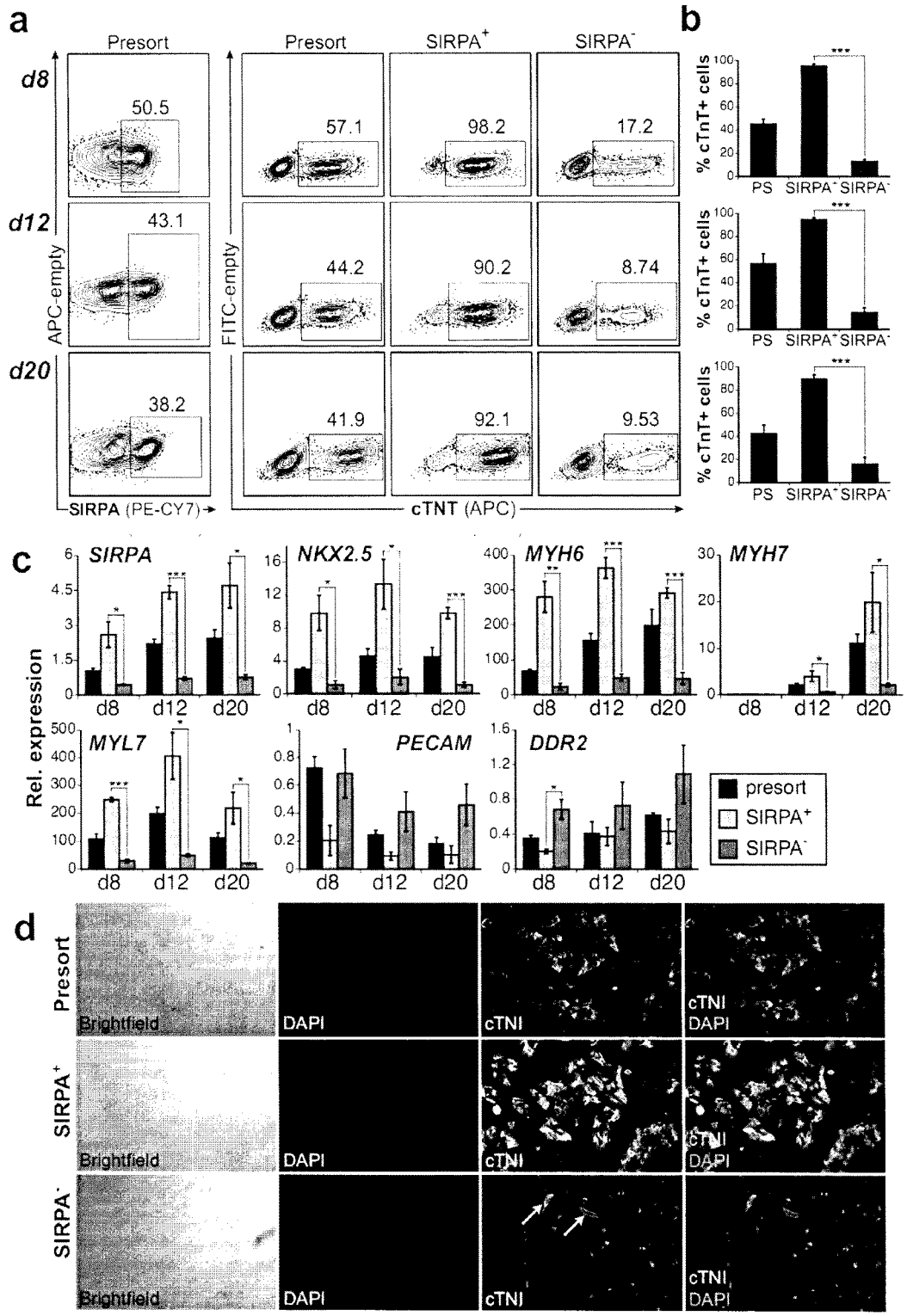
FIG. 3 shows enrichment of cardiomyocytes from hESC-derived cultures by cell sorting based on SIRPA expression. (a) Flow cytometric analysis of SIRPA expression in EBs at d8, d12 and d20 of differentiation. Fluorescent-activated cell sorting (FACS) for SIRPA was performed at d8, d12 and d20. The presort (PS), SIRPA$^+$ and SIRPA$^-$ fractions from each time point were analyzed for cardiac Troponin T (cTNT) expression by intracellular flow cytometry. The frequency of cTNT$^+$ cells at d8, d12 and d20 was significantly higher in the SIRPA$^+$ fraction (day8: 95.2%±1.9, day12: 94.4±1.7, day20: 89.6±3.6), compared to SIRPA$^-$ cells (day8: 13.0±2.1, day12: 14.3±3.9, day20: 15.7±6.0). (b) Average enrichment of cTNT$^+$ cells from 3 different cell separation experiments. Bars represent standard error of the mean. Asterisks indicate statistical significance as determined by student's t-test, ***($p \leq 0.001$) (c) QPCR analysis of PS, SIRPA$^+$ and SIRPA$^-$ cells. Expression of SIRPA, NKX2-5, MYH6, MYH7 and MYL7 was significantly higher in the SIRPA$^+$ fraction compared to SIRPA$^-$ fraction at all stages analyzed (d8, d12 and d20). Expression of markers for the non-cardiac lineages (PECAM and DDR2) segregated to the SIRPA$^-$ fraction. Bars represent mean±standard error of the mean. Asterisks indicate statistical significance as determined by student's t-test, *($p \leq 0.05$), ($p \leq 0.01$), *($p \leq 0.001$), n=3. (d) Immunostaining of cardiac Troponin I (cTNI) on monolayer cultures generated from PS, SIRPA$^+$ and SIRPA$^-$ cells sorted at day20.

To assess whether expression of the SIRPA surface receptor can be used to generate enriched populations of cardiomyocytes, SIRPA-positive (SIRPA$^+$) and SIRPA-negative (SIRPA$^-$) fractions were isolated by cell sorting from HES2-derived EBs at days 8, 12 and 20 of differentiation and analyzed for expression of cardiac Troponin T (cTNT) by intracellular flow cytometry (FIG. 3a). Analyses of the presort (unsorted, PS) populations demonstrated that cTNT expression closely paralleled that of SIRPA at the corresponding stages during differentiation (PS: d8, d12, d20). Following sorting, the SIRPA$^+$ fractions from each stage were highly enriched for cTNT$^+$ cardiomyocytes, whereas the SIRPA$^-$ fractions were depleted of these cells. It is unclear if the low numbers of cTNT$^+$ cells present in the SIRPA$^-$ fractions are contaminants from the sorting procedure or represent true SIRPA-negative cardiomyocytes. FACS based separation in multiple experiments reproducibly yielded significantly enriched populations of cardiomyocytes (SIRPA$^+$: day8 (95.2%±1.9), day12 (94.4%±1.7), day20 (89.6%±3.6); SIRP$^-$: day8 (13.0%±2.1), day12 (14.3%±3.9), day20 (15.7%±6.0))(FIG. 3b). The purity of the SIRPA$^+$ and SIRPA$^-$ sorted populations and the efficiency of cell recovery from the sorting procedure is summarized in FIG. 15 and FIG. 20 (Table 1).

Molecular analyses revealed that the SIRPA$^+$ cells expressed significantly higher levels of NKX2-5, MYH6, MYH7 and MYL7 than the SIRPA⁻ population (FIG. 3c), further demonstrating enrichment of cardiomyocytes. As expected, SIRPA expression segregated to the SIRPA⁺ population. In contrast to the cardiac markers, non-myocyte markers such as the fibroblast markers DDR2 and THY1 (CD90, data not shown) and the endothelial marker PECAM (CD31) were expressed at higher levels in the SIRPA⁻ population (FIG. 3c).

When plated in monolayer cultures, cells from both SIRPA⁻ and SIRPA⁺ fractions formed viable populations that could easily be maintained for several weeks. Contracting cells were detected in unsorted (PS) and SIRPA⁺-derived populations, but not in the population generated from the SIRPA⁻ cells. Immunohistochemical analysis revealed broad cTNI expression in the SIRPA⁺ population confirming the high proportion of cardiomyocytes in these cultures. Only few cTNI-positive cells were detected in the SIRPA⁻ population (FIG. 3d)

As anticipated from the co-expression of SIRPA and NKX2-5-GFP, it was also possible to isolate populations enriched for cardiac lineage cells from NKX2-5-GFP HES3-derived cultures by sorting with the anti-SIRPA antibody. Cardiac precursors (day 8) and cardiomyocytes (days 12 and 20) defined by gene expression and cTNT staining, segregated to the SIRPA⁺ fraction whereas non-myocyte cells were enriched in the SIRPA⁻ population (FIG. 16).

To enable rapid processing of large numbers of cells, we also attempted to isolate SIRPA cells by magnetic bead sorting. Isolation of SIRPA⁺ cells from NKX2-5-GFP differentiation cultures by this approach resulted in populations highly enriched for cardiomyocytes similar to those derived from FACS experiments (FIG. 17a-c). However, with current magnetic bead sorting protocols a substantial amount of cells is lost during the process, resulting in a lower efficiency of this approach compared to FACS (compare FIG. 17d to FIG. 20 (Table 1)).

Figure 4:
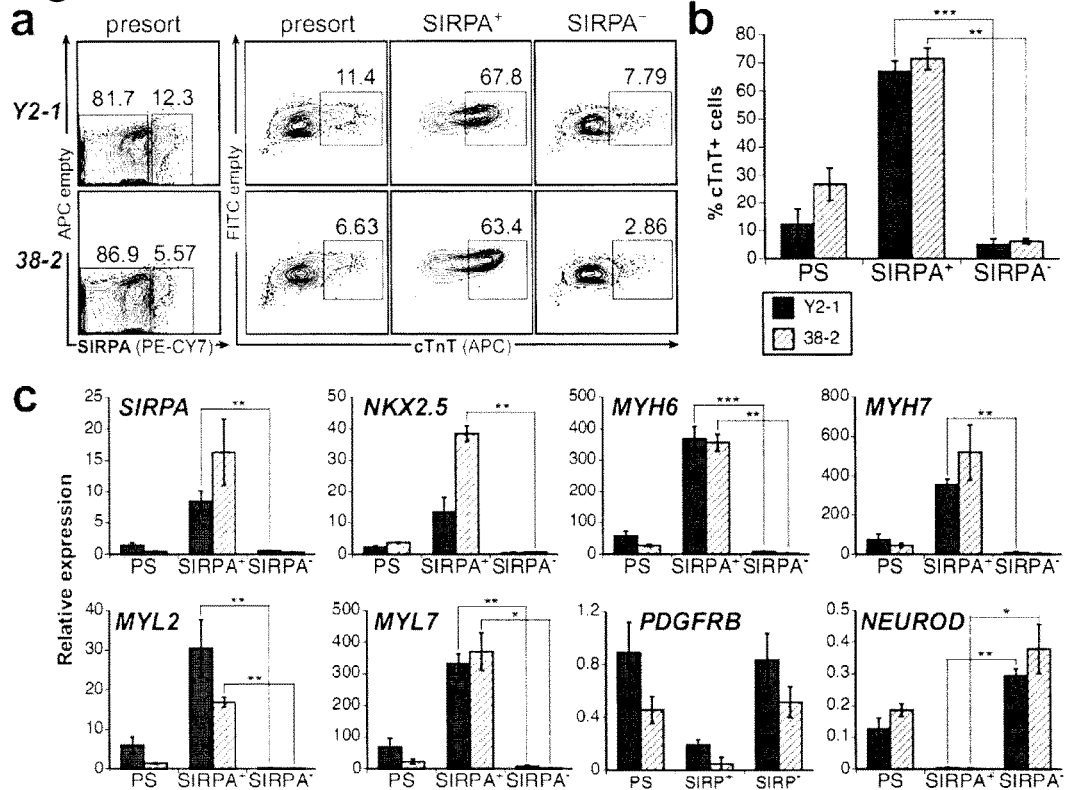
FIG. 4 shows enrichment of cardiomyocytes from hiPSC-derived cultures by cell sorting based on SIRPA expression. (a) Flow cytometric analysis of SIRPA expression at d20 of differentiation on 38-2 and MSC-iPS1 hiPSC-derived cells. Fluorescent-activated cell sorting (FACS) for SIRPA was performed at d20 and the presort (PS), SIRPA$^+$ and SIRPA$^-$ fractions were analyzed for cardiac Troponin T (cTNT) expression by intracellular flow cytometry. (b) The frequency of cTNT$^+$ cells was significantly higher in the SIRPA$^+$ fraction of both hiPSC-derived cultures (MSC-iPS1: 67.0±3.6, 38-2: 71.4±3.8), compared to SIRPA$^-$ cells (MSC-iPS1: 4.9±2.1, 38-2: 6.2±0.9). Bars represent mean±standard error of the mean. Asterisks indicate statistical significance as determined by student's t-test, ($p \leq 0.01$), *($p \leq 1.001$), n=3. (c) QPCR analysis of PS, SIRPA$^+$ and SIRPA$^-$ cells derived form MSC-iPS1 and 38-2 hiPSCs after cell sorting at d20. Expression of markers specific for the cardiac lineage (SIRPA, NKX2-5, MYH6, MYH7, MYL2 and MYL7) was significantly higher in the SIRPA$^+$ compared to the SIRPA$^-$ fraction. Expression of markers for the non-cardiac lineages (DDR2, PDGFRB and NEUROD1) segregated to the SIRPA$^-$ fraction and the PS cells. Bars represent mean±standard error of the mean. Asterisks indicate statistical significance as determined by student's t-test, *($p \leq 0.05$), ($p \leq 0.01$), *($p \leq 0.001$), n=5.

Taken together, the findings from these cell sorting studies clearly demonstrate that SIRPA expression marks the cardiac lineage in hESC-derived differentiation cultures and that cell sorting with the anti-SIRPA antibody allows for the isolation of populations highly enriched for cardiomyocytes.
Purification of Cardiomyocytes from Human Induced Pluripotent Stem Cells To determine if SIRPA expression marked the cardiac lineage in other hPSC-derived populations, we next analyzed EBs generated from two different hiPSC lines, MSC-iPS1 (also known as Y2-1) and 38-2[13,14]. The efficiency of cardiac differentiation from both lines was low, as demonstrated by the proportion of cTNT⁺ cells (MSC-iPS1: 12.2%±5.6, 38-2: 26.7%±5.7; FIG. 4a). Similar low levels of SIRPA expression were detected in both EB populations. FACS of the SIRPA⁺ cells from both iPSC lines yielded populations significantly enriched for cTNT⁺ cardiomyocytes (SIRPA⁺: MSC-iPS1 (67.0%±3.6), 38-2(71.4%±3.8); SIRPA⁻: MSC-iPS1 (4.9%±2.1), 38-2(6.2%±0.9)) (FIG. 4a,b). These SIRPA⁺ populations expressed significantly higher levels of NKX2-5, MYH6, MYH7, MYL2 and MYL7 than the corresponding SIRPA⁻ cells. As observed with the hESC-derived cells, non-myocyte markers including DDR2, PDGFRB, THY1 and NEUROD segregated to the SIRPA⁻ fraction (FIG. 4b,c and data not shown).

These data clearly document the utility of this marker for generating enriched cardiac populations from a range of pluripotent stem cell lines, including those that do not differentiate efficiently to the cardiac lineage with the current protocols.

SIRPA Expression in Human Fetal and Adult Heart Cells

Figure 5:
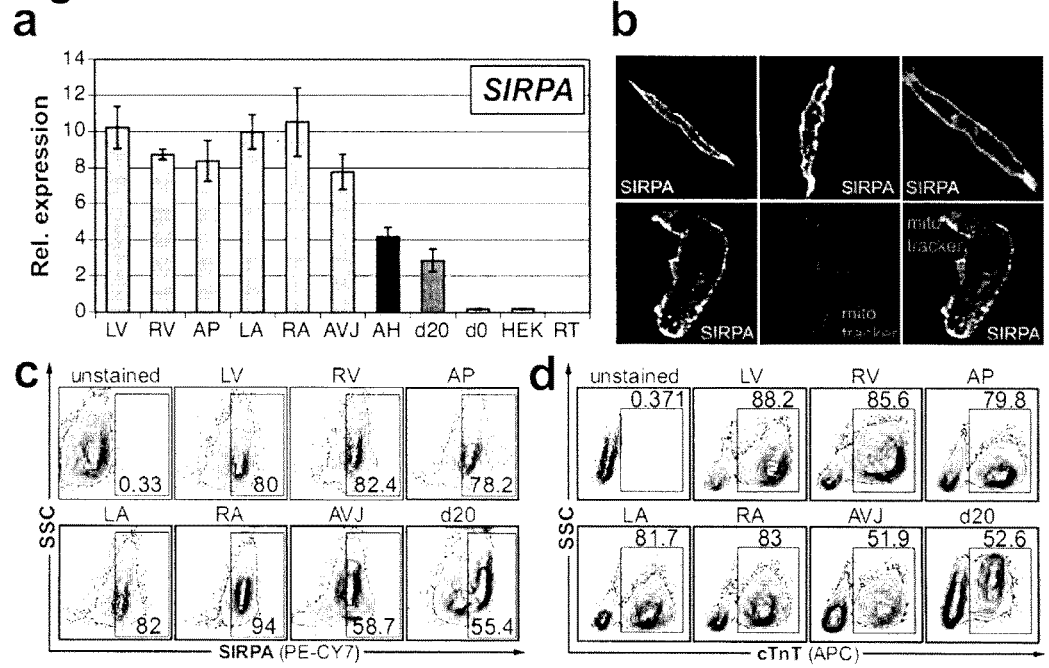
FIG. 5 shows expression of SIRPA on human fetal cardiomyocytes and in adult human heart. (a) RT-qPCR analysis for SIRPA in human fetal heart tissue and adult heart. LV, left ventricle; RV, right ventricle; AP, Apex; LA, left atria; RA, right atria, AVJ, atrioventricular junction; HEK, human embryonic kidney cells; AH, adult heart; day 0, hES cells; d20, day20 of cardiac differentiation, RT, reverse transcriptase control. Bars represent mean±standard error of the mean, n=6. (b) Immunostaining for SIRPA (green) on human fetal ventricular cells and staining with Mito Tracker Red (red, accumulates in the mitochondrial matrix) and DAPI (blue, nuclear dye). (c) Flow cytometric analysis for SIRPA on human fetal heart tissue. (d) Intracellular flow cytometric analysis for cTNT on human fetal heart tissue.

To determine if SIRPA is expressed on primary human cardiomyocytes, we next analyzed expression patterns in fetal (18-20 weeks of gestation) and adult heart tissue by RT-qPCR. As shown in FIG. 5a, SIRPA transcripts were detected in all fetal-derived heart tissue (left (LA) and right atrial (RA) cells, left (LV) and right ventricle (RV) cells, apex (AP) and atrioventricular junction (AVJ)), with comparable levels to those found in day 20 hESC-derived cells (FIG. 3a). SIRPA was not expressed in undifferentiated hESCs (d0) or in control HEK (human embryonic kidney) cells. Similar to the fetal heart, SIRPA expression was also detected in the adult heart, suggesting that its expression marks cardiomyocytes at different stages of human cardiac development. High levels of SIRPA were detected in the adult human brain and lung (FIG. 18a) with low levels found in many other tissues. These low levels may reflect the presence of tissue macrophages that are known to express this receptor[15,16]. CD47, the SIRPA ligand was expressed in most tissues, confirming the pattern described in previous studies (FIG. 18b)[15]. Immunofluorescence staining showed that SIRPA was localized on the surface membrane of the fetal ventricular cells but was not present on other membrane fractions such as the mitochondrial membrane, as indicated by the lack of co-staining with Mito Tracker Red (FIG. 5b). Flow cytometric analyses revealed a high proportion of SIRPA⁺ cells in all fetal heart tissues at levels that correlated with the percentage of cTNT⁺ cells in the respective fractions (FIG. 5c, d).

Figure 6:
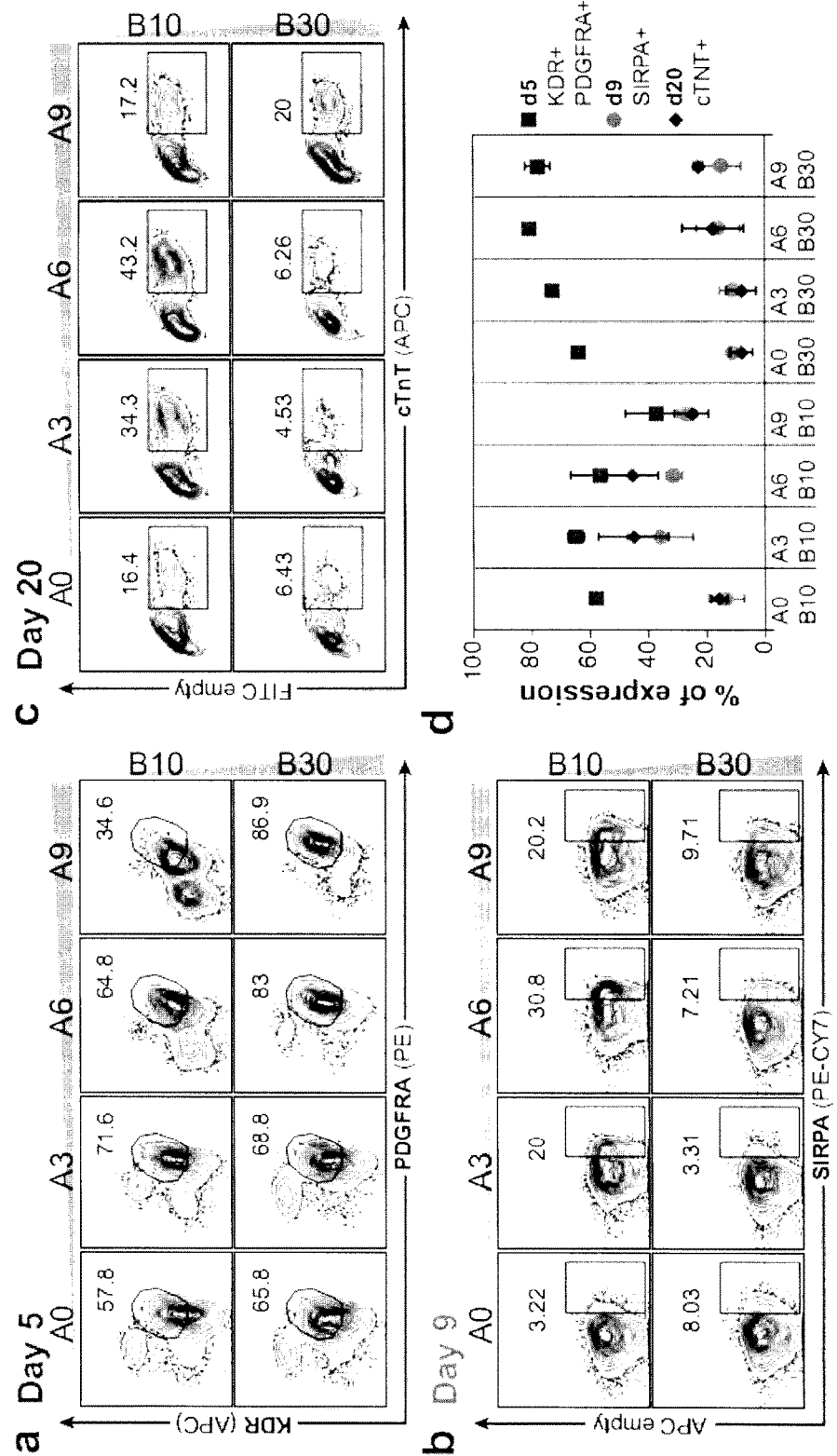
FIG. 6 shows the utilization of SIRPA to predict cardiac differentiation efficiency. (a) Day5 KDR/PDGFRA flow cytometry profiles of cardiac differentiation cultures induced with varying combinations of Activin A (ACTA0, 3, 6, 9 ng/ml) and BMP4 (10, 30 ng/ml). The KDR$^+$PDGFRB$^+$ population has been shown to contain the cardiac mesoderm cells[2]. (b) Day 9 SIRPA flow cytometric analysis expression profiles of the cultures described in (a). (c) Day 20 cTNT profiles (intracellular flow cytometric analysis) of the cultures described in (a). (d) Quantification of a-c. Close correlation of expression of SIRPA at day 9 (green dots) and cTNT expression at day20 (red rhombuses) illustrates the predictive potential of SIRPA for cardiac differentiation efficiency.
Figure 7:
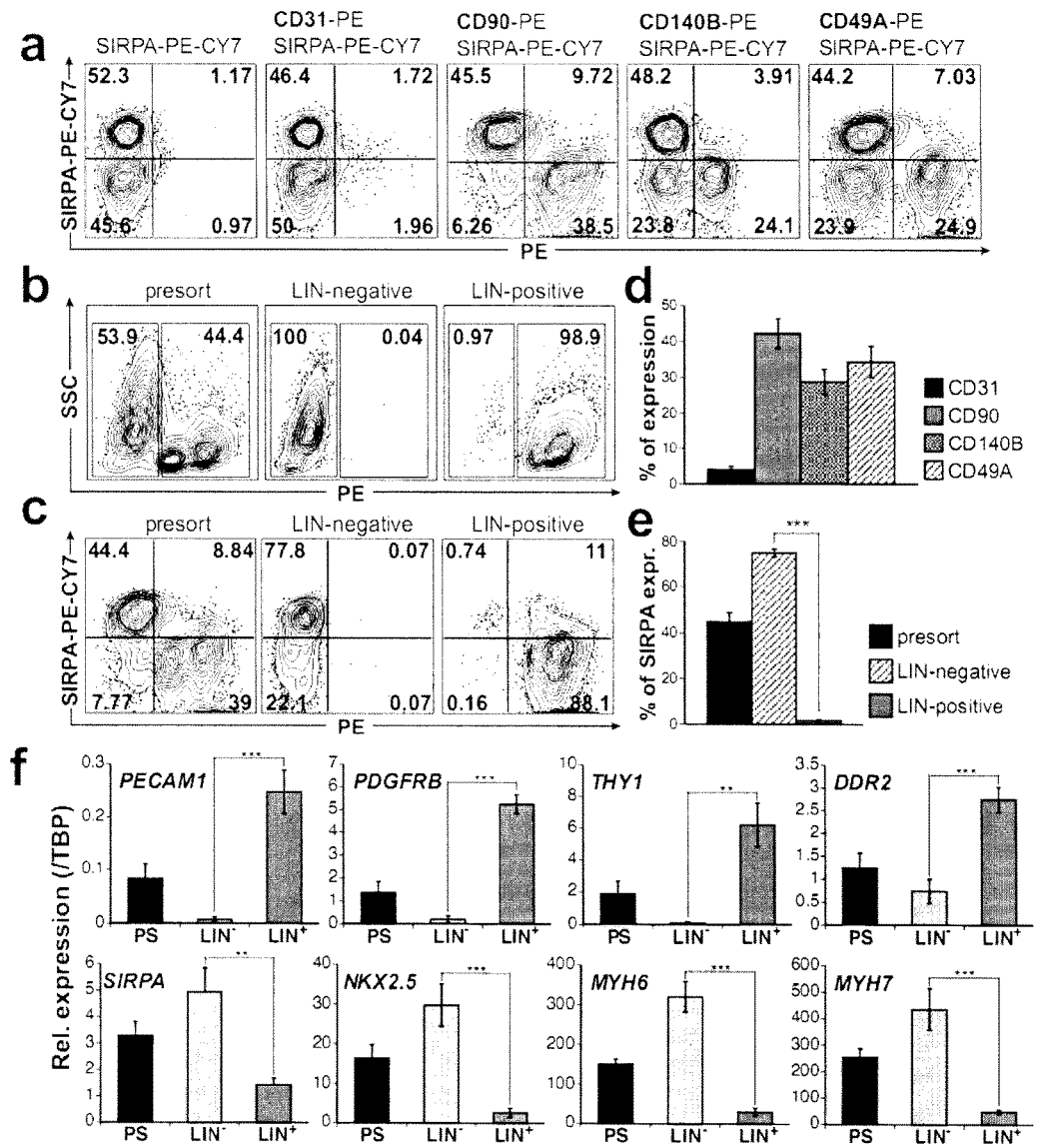
FIG. 7 shows enrichment of cardiomyocytes through negative selection. (a) Flow cytometric analysis of markers specifically expressed on non-myocyte (SIRPA-negative) cells in day 20 differentiation cultures (HES2). (b) Fluorescent activated cell sorting for the combination of markers specifically expressed on non-myocyte cells (in PE: CD31, CD90, CD140B, CD49A). (c) Flow cytometric analysis of the presort cells, PE-negative (LIN$^-$) and PE-positive (LIN$^+$) samples for SIRPA. (d) Quantification of non-myocyte markers in at day20 of differentiation (as shown in (a)), n=4. (e) Quantification of SIRPA-positive cells in PS, LIN– and LIN+ fractions after cell sorting. Asterisks indicate statistical significance as determined by student's t-test, *** ($p \leq 0.001$), n=3. (f) QPCR analysis of the presort (PS), LIN$^-$ and LIN$^+$ samples for non-cardiac markers (PECAM1, PDGFRB, THY1 and DDR2) and cardiac specific genes (SIRPA, NKX2-5, MYH6 and MYH7). Bars represent mean±standard error of the mean. Asterisks indicate statistical significance as determined by student's t-test, *($p \leq 0.05$), ($p \leq 0.01$), *($p \leq 0.001$), n=3.

These findings demonstrate clearly that SIRPA is expressed on fetal cardiomyocytes as well as in adult heart, illustrating that its cardiac-specific expression is not an artifact of pluripotent stem cell-derived cultures.
Using SIRPA Expression to Monitor the Efficiency of hPSC Differentiation Recently, we reported that co-expression of KDR and PDGFRA provides a reliable method to monitor cardiac mesoderm induction following treatment with BMP4 and Activin A[2] (FIG. 6a). While this study showed that the induction of a KDR⁺PDGFRA⁺ population was an essential first step in the generation of the cardiomyocyte population, not all KDR⁺PDGFRA⁺ populations differentiated to give rise to cardiac lineage cells (example of this type of population: induced with 30 ng/ml BMP4 and no exogenous Activin A (A0)). To determine if SIRPA would more accurately predict cardiac potential of differentiating populations at an early stage, we monitored its expression in day 9 EBs induced with different concentrations of Activin A and BMP4 (FIG. 6b). The same populations were evaluated at day 5 for expression of KDR and PDGFRA (FIG. 6a) and at day 20 for expression of cTNT (FIG. 6c). While there was little correlation between the size of the KDR⁺PDGFRA⁺ population at day 5 and the proportion of cTNT⁺ cells at day 20, the cultures with the largest SIRPA population at day 9 (Activin A 6 ng/ml, BMP4 10 ng/ml) contained the highest number of cTNT⁺ cells at the later time point. SIRPA expression correlated well with cTNT output for most conditions tested and the highest levels of SIRPA predicted the highest cardiomyocyte development at day 20 (FIG. 6d). These data demonstrate that expression of SIRPA at day 9 is a reliable indicator of cardiomyocyte potential, and as such can be used to monitor and optimize induction protocols for directed differentiation of hPSCs to the cardiac lineage.
Enrichment of hPSC-Derived Cardiomyocytes Through Depletion of the Non-Myocyte Lineage Cells In addition to antibodies that recognize cardiomyocytes, our flow cytometric screen also identified a panel of antibodies that marked the non-myocyte population in the differentiation cultures. This set of antibodies, including anti-CD90 (THY1, expressed on fibroblast cells), anti-CD31 (PECAM1, expressed on endothelial cells), anti-CD140B (PDGFRB, expressed on smooth muscle cells) and anti-CD49A (INTEGRIN1A), all recognized different proportions of the SIRPA$^-$ population of day 20 HES2-derived EBs (FIG. 7a/d). The combination of these antibodies marked the majority of non-myocyte (SIRPA$^-$) cells in the culture (FIG. 7c, presort). To determine if it was possible to enrich for cardiomyocytes by depleting cells expressing the non-myocyte markers, we combined these antibodies and sorted day 20 EBs into lineage-positive (LIN$^+$) and lineage-negative (LIN$^-$) fractions (FIG. 7b). This approach has the advantage in generating enriched populations free of any bound antibody or magnetic beads. As expected, the LIN$^-$ population was significantly enriched for SIRPA$^+$ cells, whereas the LIN$^+$ population was depleted for the cardiomyocytes (FIG. 7c/e). The efficiency of cell recovery after FACS for LIN$^-$ and LIN$^+$ cells is summarized in FIG. 21 (Table 2). Gene expression analyses revealed that non-myocyte specific genes including PECAM1, PDGFRB, THY1 and DDR2 were primarily expressed in the LIN$^+$ fraction, whereas cardiac gene expression was restricted to the LIN$^-$ fraction (FIG. 7f). When plated on gelatin coated dishes or re-aggregated as cell clusters, the LIN$^-$ fraction generated populations that contained a high proportion of contracting cardiomyocytes (data not shown). The same lineage cocktail of antibodies also marked the non-myocyte (SIRPA–) fraction of the iPSC (MSC-iPS1)-derived day 20 EB population (FIG. 19), indicating that this depletion approach can be applied to different PSC lines with variable differentiation efficiencies.

Taken together, these data illustrate that cardiomyocytes can be enriched from hPSC-derived differentiation cultures by depletion of the non-myocyte lineages. This method therefore represents an alternative approach to obtaining highly purified cardiomyocyte cultures and may as such be used for strategies that require purified cardiomyocyte populations free of any bound antibodies.

Advances in our understanding of the signaling pathways that regulate lineage specification has led to strategies for the efficient and reproducible directed differentiation of hPSCs to specific cell types[1]. With respect to cardiac lineage development, protocols have been established that promote the generation of mixed cardiovascular populations representing the major cell types found in the human heart including cardiomyocytes, endothelial cells, vascular smooth muscle cells and fibroblasts. Cardiomyocytes typically represent between 10% and 70% of such mixed populations[2,3], depending on the PSC line used. While such mixed populations have been used to demonstrate the potential utility of the PSC-derived cells for predictive toxicology[5], modeling human disease in vitro[17,18] and transplantation based therapy for heart disease[19], highly enriched and well defined cell populations will ultimately be required to translate this potential into practical applications.

Our identification of SIRPA as a cardiomyocyte-specific marker now enables, for the first time, easy and routine access to highly enriched populations of cardiomyocytes from hESCs and hiPSCs. These cardiomyocyte enriched populations can be isolated by FACS or magnetic bead sorting, the latter approach enabling the isolation of large numbers of cells required for in vivo studies. Access to highly enriched populations of cardiomyocytes through simple sorting approaches will enable the development of defined high throughput drug discovery and toxicology assays, the detailed phenotypic evaluation of cells generated from patient specific hPSCs, and the generation of defined populations safe for transplantation. The fact that SIRPA is expressed on cardiac lineage cells from the earliest cardiac stage to contracting and more mature cardiomyocytes will allow for comparisons of the in vivo potential of the different populations.

In addition to SIRPA, our screen also identified a panel of markers defining the non-myocyte fractions of the PSC-derived cardiovascular population. The markers used suggest that they represent a combination of fibroblasts (CD90, THY1)[20], vascular smooth muscle cells (CD140B, PDGFRB)[21] and endothelial cells (CD31, PECAM1). Access to enriched populations of each of these cell types together with cardiomyocytes will allow. Many of the proposed applications for PSC-derived cardiomyocytes may require three-dimensional engineered tissue to more accurately reflect drug responses and function in the adult heart. Recent studies suggest that appropriate combinations of cardiac cells, endothelial cells and fibroblasts need to be incorporated into such tissue constructs in order for them to function best in vitro or in vivo[22-24]. Our ability to generate pure myocyte and non-myocyte populations will allow for the generation of engineered constructs consisting of varying proportions of different cell types, enabling us to determine the optimal proportion of each required to form heart tissue with structural and functional properties most similar to that of the human heart.

The specific expression pattern of SIRPA in the PSC-derived populations and in the fetal heart tissue suggests that this receptor plays some functional role in the human cardiomyocyte lineage, perhaps as early as the precursor stage of development. The fact that expression of the ligand, CD47, is upregulated in parallel with SIRPA in the EBs and that CD47 is found on a large proportion of the cells in the culture further supports the interpretation that this ligand/receptor pair plays a role in the human cardiomyocyte development and/or function. One thoroughly studied role for SIRPA is on macrophages, where it appears to mediate a signal to eliminate cells from the body that do not express the ligand CD47[16]. The only other suggested function in human cells is in the smooth muscle lineage, where SIRPA has been shown to play an important role in mediating IGF-1-induced mitogenic signaling[25]. Given that SIRPA was not detected in mouse cardiomyocytes, it is possible that its function in human cells may relate to aspects of cardiomyocyte physiology and/or function that differ between the two species.

In summary, the findings reported here demonstrate that expression of SIRPA uniquely marks the cardiomyocyte lineage in PSC-differentiation cultures. Isolation of SIRPA$^+$ cells by FACS or magnetic bead sorting provides a simple approach for generating highly enriched populations of cardiomyocytes from a broad range of PSC lines, including those that do not differentiate efficiently to the cardiovascular lineage using current protocols.

Although preferred embodiments of the invention have been described herein, it will be understood by those skilled in the art that variations may be made thereto without departing from the spirit of the invention or the scope of the appended claims. All references in this description, including those in the following reference list, are hereby incorporated by reference.

REFERENCE LIST

1 Murry, C. E. & Keller, G. Differentiation of embryonic stem cells to clinically relevant populations: lessons from embryonic development. *Cell* 132, 661-680, (2008).

2 Kattman, S. J. et al. Stage-specific optimization of activin/nodal and BMP signaling promotes cardiac differentiation of mouse and human pluripotent stem cell lines. *Cell Stem Cell* 8, 228-240, (2011).

3 Yang, L. et al. Human cardiovascular progenitor cells develop from a KDR+ embryonic-stem-cell-derived population. *Nature* 453, 524-528, (2008).

4 Zwi, L. et al. Cardiomyocyte differentiation of human induced pluripotent stem cells. *Circulation* 120, 1513-1523, (2009).

5 Braam, S. R., Passier, R. & Mummery, C. L. Cardiomyocytes from human pluripotent stem cells in regenerative medicine and drug discovery. *Trends Pharmacol Sci* 30, 536-545, (2009).

6 Anderson, D. et al. Transgenic enrichment of cardiomyocytes from human embryonic stem cells. *Mol Ther* 15, 2027-2036, (2007).

7 Huber, I. et al. Identification and selection of cardiomyocytes during human embryonic stem cell differentiation. *FASEB J* 21, 2551-2563, (2007).

8 Ritner, C. et al. An engineered cardiac reporter cell line identifies human embryonic stem cell-derived myocardial precursors. *PLoS One* 6, e16004, (2011).

9 Hattori, F. et al. Nongenetic method for purifying stem cell-derived cardiomyocytes. *Nat Methods* 7, 61-66, (2010).

10 Seiffert, M. et al., Signal-regulatory protein alpha (SIRPalpha) but not SIRPbeta is involved in T-cell activation, binds to CD47 with high affinity, and is expressed on immature CD34(+)CD38(−) hematopoietic cells. *Blood* 97, 2741-2749, (2001).

11 Timms, J. F. et al. SHPS-1 is a scaffold for assembling distinct adhesion-regulated multi-protein complexes in macrophages. *Curr Biol* 9, 927-930, (1999).

12 Subramanian, S., Parthasarathy, R., Sen, S., Boder, E. T. & Discher, D. E. Species- and cell type-specific interactions between CD47 and human SIRPalpha. *Blood* 107, 2548-2556, (2006).

13 Nostro, M. C. et al. Stage-specific signaling through TGFbeta family members and WNT regulates patterning and pancreatic specification of human pluripotent stem cells. *Development* 138, 861-871, (2011).

14 Park, I. H. et al. Reprogramming of human somatic cells to pluripotency with defined factors. *Nature* 451, 141-146, (2008).

15 Matozaki, T., Murata, Y., Okazawa, H. & Ohnishi, H. Functions and molecular mechanisms of the CD47-SIRPalpha signalling pathway. *Trends Cell Biol* 19, 72-80, (2009).

16 Okazawa, H. et al. Negative regulation of phagocytosis in macrophages by the CD47-SHPS-1 system. *J Immunol* 174, 2004-2011, (2005).

17 Carvajal-Vergara, X. et al. Patient-specific induced pluripotent stem-cell-derived models of LEOPARD syndrome. *Nature* 465, 808-812, (2010).

18 Itzhaki, I. et al. Modelling the long QT syndrome with induced pluripotent stem cells. *Nature* 471, 225-229, (2011).

19 Laflamme, M. A. et al. Cardiomyocytes derived from human embryonic stem cells in pro-survival factors enhance function of infarcted rat hearts. *Nat Biotechnol* 25, 1015-1024, (2007).

20 Kisselbach, L., Merges, M., Bossie, A. & Boyd, A. CD90 Expression on human primary cells and elimination of contaminating fibroblasts from cell cultures. *Cytotechnology* 59, 31-44, (2009).

21 Ross, R. The pathogenesis of atherosclerosis: a perspective for the 1990s. *Nature* 362, 801-809, (1993).

22 Stevens, K. R. et al. Physiological function and transplantation of scaffold-free and vascularized human cardiac muscle tissue. *Proc Natl Acad Sci USA* 106, 16568-16573, (2009).

23 Dvir, T. et al. Prevascularization of cardiac patch on the omentum improves its therapeutic outcome. *Proc Natl Acad Sci USA* 106, 14990-14995, (2009).

24 Lesman, A. et al. Transplantation of a tissue-engineered human vascularized cardiac muscle. *Tissue Eng Part A* 16, 115-125, (2010).

25 Ling, Y., Maile, L. A., Lieskovska, J., Badley-Clarke, J. & Clemmons, D. R. Role of SHPS-1 in the regulation of insulin-like growth factor I-stimulated Shc and mitogen-activated protein kinase activation in vascular smooth muscle cells. *Mol Biol Cell* 16, 3353-3364, (2005).

26 Kennedy, M., D'Souza, S. L., Lynch-Kattman, M., Schwantz, S. & Keller, G. Development of the hemangioblast defines the onset of hematopoiesis in human ES cell differentiation cultures. *Blood* 109, 2679-2687, (2007).

27 Costa, M. et al. A method for genetic modification of human embryonic stem cells using electroporation. *Nat Protoc* 2, 792-796, (2007).

28 Sharma, P., Shathasivam, T., Ignatchenko, V., Kislinger, T. & Gramolini, A. O. Identification of an FHL1 protein complex containing ACTN1, ACTN4, and PDLIM1 using affinity purifications and MS-based protein-protein interaction analysis. *Mol Biosyst* 7, 1185-1196, (2011).

29 Seiffert, M. et al. Human signal-regulatory protein is expressed on normal, but not on subsets of leukemic myeloid cells and mediates cellular adhesion involving its counterreceptor CD47. *Blood* 94, 3633-3643, (1999).

The invention claimed is:

1. An in vitro method of selecting human cardiomyocyte progenitors, human cardiomyocytes, or both, from a population of cells comprising human cardiomyocyte progenitors, human cardiomyocytes, or both, which are derived from human embryonic stem cells (ESCs) or human induced pluripotent stem cells (iPSCs), the method comprising:

contacting the population of cells with a signal-regulatory protein alpha (SIRPA)-specific ligand which specifically binds SIRPA expressed on the surface of SIRPA$^+$ cardiomyocyte progenitors and SIRPA$^+$ cardiomyocytes;

sorting the cell population based on binding of the SIRPA ligand to SIRPA$^+$ cardiomyocyte progenitors or SIRPA$^+$ cardiomyocytes, or both; and selecting SIRPA$^+$ cardiomyocyte progenitors or SIRPA$^+$ cardiomyocytes, or both, from the sorted cell population.

2. The method of claim 1, further comprising depleting cells from the population of cells, which express at least one of the following cell surface markers: CD90, CD31, CD1406 and CD49A before selecting SIRPA$^+$ cardiomyocyte progenitors or SIRPA$^+$ cardiomyocytes, or both.

3. The method of claim 2, wherein the cells expressing at least one of CD90, CD31, CD1406 and CD49A are depleted using a corresponding antibody.

4. The method of claim 1, wherein the SIRPA-specific ligand is selected from the group consisting of an anti-SIRPA antibody, an anti-SIRPA antibody fragment, and an anti-SIRPA antibody-like molecule.

5. The method of claim 1, wherein the cardiomyocyte progenitors or cardiomyocytes, or both, SIRPA are sorted using at least one method selected from the group consisting of fluorescence activated cell sorting, magnetic separation using antibody-coated magnetic beads, affinity chromatography, and exploitation of differences in physical properties.

6. The method of claim 1, wherein the selected cells comprise at least 60%, at least 90%, or at least 95% cardiomyocyte cells, cardiomyocyte progenitor cells, or both.

7. A SIRPA$^+$ human cardiomycotye progenitor or human cardiomyocyte according to claim 1, wherein the SIRPA-specific ligand is bound to the SIRPA protein expressed on the surface of the cardiomyocyte progenitor or cardiomyocyte.

8. The method of claim 1, wherein the human cardiomyocytes are contracting cardiomyocytes.

9. The method of claim 1, wherein the human cardiomyocyte progenitors, human cardiomyocytes, or both, express cardiac-specific structural proteins.

10. The method according to claim 1, wherein the human cardiomyocyte progenitors, human cardiomyocytes, or both, are derived from embryonic stem cells.

11. The method according to claim 1, wherein the human cardiomyocyte progenitors, human cardiomyocytes, or both, are derived from induced pluripotent stem cells.

12. An in vitro method of depleting human cardiomyocyte progenitors, human cardiomyocytes, or both, from a population of cells comprising human cardiomyocyte progenitors, human cardiomyocytes, or both, which are derived from human embryonic stem cells (ESCs) or human induced pluripotent stem cells (iPSCs), the method comprising:

contacting the population of cells with a signal-regulatory protein alpha (SIRPA)-specific ligand which specifically binds SIRPA expressed on the surface of SIRPA$^+$ cardiomyocyte progenitors and SIRPA$^+$ cardiomyocytes;

sorting the cell population based on binding of the SIRPA ligand to SIRPA$^+$ cardiomyocyte progenitors or SIRPA$^+$ cardiomyocytes, or both; and depleting SIRPA$^+$ cardiomyocyte progenitors or SIRPA$^+$ cardiomyocytes, or both, from the sorted cell population.

* * * * *